(12) United States Patent
Liu et al.

(10) Patent No.: US 6,277,330 B1
(45) Date of Patent: Aug. 21, 2001

(54) OPTICAL SENSOR FOR DETECTING CHEMICAL SUBSTANCES DISSOLVED OR DISPERSED IN WATER

(75) Inventors: Yuan Liu, Knoxville, TN (US); Hironobu Yamamoto, Sayama; Akihiro Tagaya, Yokohama, both of (JP)

(73) Assignee: Aventis Research & Technologies GmbH & Co K.G. (DE)

(*) Notice: Subject to any disclaimer, the term of this patent is extended or adjusted under 35 U.S.C. 154(b) by 0 days.

(21) Appl. No.: 09/269,433

(22) PCT Filed: Sep. 30, 1997

(86) PCT No.: PCT/EP97/05361

§ 371 Date: Oct. 4, 1999

§ 102(e) Date: Oct. 4, 1999

(87) PCT Pub. No.: WO98/14771

PCT Pub. Date: Apr. 9, 1998

(30) Foreign Application Priority Data

Sep. 30, 1996 (JP) ................................................ 8-259439
Jun. 13, 1997 (EP) ................................................ 97109658

(51) Int. Cl.[7] .................................................. G01N 21/45
(52) U.S. Cl. .................................. 422/82.05; 422/82.09; 356/355
(58) Field of Search ........................... 422/82.05, 82.09; 356/355, 356

(56) References Cited

U.S. PATENT DOCUMENTS

| | | | |
|---|---|---|---|
| 2,666,355 | * 1/1954 | Trurnit . | |
| 4,940,328 | 7/1990 | Hartman | 356/345 |
| 5,015,843 | * 5/1991 | Seitz et al. | 250/227.21 |
| 5,120,505 | * 6/1992 | Lowell, Jr. et al. | 422/58 |
| 5,341,215 | * 8/1994 | Seher | 356/445 |
| 5,611,998 | * 3/1997 | Aussenegg et al. | 422/82.05 |
| 5,631,171 | * 5/1997 | Sandstrom et al. | 436/518 |

FOREIGN PATENT DOCUMENTS

| | | |
|---|---|---|
| 0305109 | 3/1989 | (EP) . |
| 0598341 | 5/1994 | (EP) . |
| 0720014 | 7/1996 | (EP) . |
| WO 93/01487 | 1/1993 | (WO) . |

OTHER PUBLICATIONS

Krska, R., et al, *Applied Physics Letters 61* : 1778–1780 (1992).
Krska, R., et al, *Applied Physics Letters 63* : 1868–1870 (1993).

* cited by examiner

*Primary Examiner*—Jeffrey Snay
(74) *Attorney, Agent, or Firm*—Connolly Bove Lodge & Hutz LLP

(57) ABSTRACT

A highly sensitive optical sensor in a simple structure for detecting a chemical substance dissolved or dispersed in water is provided. The optical sensor (1) comprises a detecting element (2) having a polymer thin film, a light source unit (3) for emitting light for irradiating the polymer thin film, and a photodetector (4) for detecting the intensity of light reflected from the polymer thin film. The detecting element (2), the light source unit (3), and the photo-detector (4) are integrally mounted in a housing. The polymer thin film is formed on a highly reflective substrate or an optically transparent substrate so as to interact with a chemical substance dissolved or dispersed in water flowing through a water channel (8).

12 Claims, 14 Drawing Sheets

OPTICAL SENSOR FOR DETECTING CHEMICAL SUBSTANCES DISSOLVED OR DISPERSED IN WATER

The present invention relates generally to an optical sensor and more particularly to an optical sensor which utilizes a polymer thin film for directly detecting a chemical substance dissolved or dispersed in water, particularly dissolved organic carbon (hereinafter abbreviated as "DOC") in accordance with an optical detecting method such as a waveguide mode method (WG method), surface plasma resonance method (SPR method), interference enhanced reflection method (IER method), and so on. The polymer thin film interacts with a chemical substance such as hydrocarbon and so on which may be absorbed into or adsorbed on the polymer thin film. As a result, the polymer thin film exhibits a change in thickness and/or refractive index depending on the concentration of the chemical substance, so that such a physical change may be measured by an optical method to determine the concentration of the chemical substance dissolved or dispersed in water, particularly, DOC.

A variety of reports have been made on the use of polymer thin films in optical sensors for detecting chemical species in gas phase and chemical substances dissolved in water. Many of these reports are related to fiber optic sensors or optical waveguide sensors based on evanescent waves or guided waves.

As is well known in the art, when a light beam is incident on an interface between two dielectric materials having different refractive indices $n_1$ and $n_2$ ($>n_1$), respectively, total internal reflection occurs when the light beam is incident from the dielectric material of the refractive index $n_1$ to the dielectric material of the refractive index $n_2$ and when the angle of incidence is larger than a critical angle $\theta c$. The critical angle $\theta c$ of total internal reflection is given by:

$$\theta c = \sin^{-1}(n_1/n_2) \quad (1)$$

In this case, the incident light is fully reflected back into the dielectric material of the refractive index $n_2$ so that no light will enter the dielectric material of refractive index $n_1$. However, there exists a wave function called an evanescent wave which propagates in parallel with the interface between the dielectric material of refractive index $n_1$ and the dielectric material of the refractive index $n_2$. The electric field E of the evanescent wave decays exponentially with the distance $\underline{z}$ from the interface, and can be expressed by an exponential function:

$$E = E_0 \exp(-z/d_p) \quad (2)$$

where $E_0$ is the electric field on the interface, and $d_p$ is the depth of penetration defined as the distance where the electric field of the evanescent wave, produced when light is incident on the interface at an angle $\theta$, is reduced from the value at the interface to 1/e, and is expressed by:

$$d_p = \lambda[2\pi(n_2^2 \sin^2 \theta - n_1^2)^{1/2}] \quad (3)$$

As is well known in the art, optical waveguides operate based on the principle of total internal reflection. A planar waveguide, which is one type of the optical waveguides, simply consists of a first medium of refractive index $n_2$ sandwiched between a second medium of refractive index $n_1$ and a third medium of refractive index $n_3$, where the refractive indices of the media are selected such that $n_2 > n_3 \geq n_1$ is satisfied. A light beam is confined in the first medium by successive total reflections when the light beam is traveling in the medium $n_2$ at an angle $\theta$ larger than the critical angle of total internal reflection on interfaces of the first medium and the two other media (in this event, $\sin \theta > n_3/n_2 \geq n_1/n_2$ is satisfied). In this case, waveguiding occurs, and the light waves existing in the first medium are called guided waves. Optical fibers are another type of waveguides consisting of a cylindrical core of refractive index $n_2$ surrounded by a cladding layer of refractive index $n_1$ ($<n_2$).

In either evanescent wave sensors or guided wave sensors, light must travel at an angle larger than the critical angle of total internal reflection. Typical examples of optical chemical sensors based on evanescent waves can be found in many prior art documents. Carter et al. disclose in USP No. Re.33064 a method of identifying a chemical species in a solvent using an optical waveguide covered with a response film having a refractive index smaller than that of the waveguide layer. Light propagates through the optical waveguide by the action of total internal reflection.

Within the propagating light, evanescent waves generated by the total reflection only are involved in interaction of the response film with a chemical species under detection. Thus, the method proposed by Carter et al. is limited only on interaction which is accompanied with absorption or scattering of light, or generation of fluorescence.

Hinrich et al. have reported the use of polymer for detecting organic compounds in water on an internal reflection element in "Determination of organic compounds by IR/ATR spectroscopy with polymer-coated internal reflection elements" (Applied Spectroscopy, Vol. 44, No. 10, 1990, pp 1641–1646). However, the detecting method of Hinrich et al. relies on the absorption of evanescent waves of infrared rays penetrating in the polymer film by organic compounds, wherein the polymer film is used to eliminate water and extract the organic compounds on the surface of the internal reflection element to thereby enhance an absorption signal.

Burck et al. have reported a similar method except for the use of an optical fiber in "A fiber optic evanescent field absorption sensor for monitoring organic contamination in water" (Fresenius J. Anal. Chem., (1994), 342, pp 394–400) and "Fiber-optic evanescent wave sensor for in situ determination of non-polar organic compounds in water" (Sensors and Actuators, B 18–19 (1994), pp 291–295).

Japanese Laid-open Patent Application No. 7-85122 (1995) discloses a method for detecting an organic solvent in water with an optical fiber having a cladding layer made of a chitosan compound. Since the intensity of evanescent waves penetrating into the chitosan cladding layer depends on the degree of swelling, and the concentration of the chitosan cladding layer varies in accordance with the ratio of water to solvent, the intensity of light propagating the optical fiber is consequently a function of the concentration of organic solvent dissolved in water.

A main disadvantage of a sensor utilizing evanescent waves, however, is that the sensitivity of the sensor is limited since only a portion of incident light is used for detection. Thus, a long interaction distance is required to realize a sensor having a high sensitivity. This imposes a limit on reduction in size of such sensors.

A larger portion of incident light may be utilized for detection to provide sensors having higher sensitivities. WO95/20151 discloses a chemical sensor having a multi-layered optical fiber. Specifically, a sensing polymer layer is sandwiched between a core of the optical fiber and a cladding layer, and the refractive index of the polymer layer is larger than that of the cladding layer so that the polymer layer serves as an optical waveguide layer. With this structure, light incident to the optical fiber is refracted toward the polymer waveguide layer and propagates therethrough toward the end terminal of the sensor. However, since this structure requires an output light detector to be located near an output terminal, the chemical sensor disclosed in WO95/20151 is inconvenient for measuring a substance to be detected in water.

A large number of highly sensitive polymers for detecting chemical substances in gas have also been reported. Gliliani et al. have reported a strip-shaped polymer waveguide having a thickness of 1 $\mu$m for detecting the existence of several kinds of organic vapors in "Fabrication of an integrated optical waveguide chemical vapor microsensor by photopolymerization of a bifunctional oligomer" (Appl. Phys. Lett., 48 (1986), pp 1311–1313) and "Integrated optical chemical vapor microsensor" (Sensors and Actuators, 15 (1988), pp 25–31). A method proposed by them involves introducing non-polarized light into a waveguide channel from one end of an optical fiber by fiber coupling, and extracting the light propagating through the waveguide from the other end to the outside. In this way, interaction between the polymer and an organic vapor is sensed as a change in intensity of the transmitting (propagating) light. The method of Gluliani et al., however, implies the following two difficulties: (1) a photopolymerized polymer is required to fabricate the strip-shaped waveguide; and (2) the strip-shaped waveguide must be coupled by end-fire coupling to a thin film having a thickness on order of micrometers.

A planar polymer thin film optical waveguide as a sensor for detecting organic vapors has been reported by Bowman and Burgess in "Evaluation of polymer thin film waveguides as chemical sensors" (SPIE Proceedings, Vol. 1368: Chemical, biochemical, and environmental II, 1990). The polymer film exhibits a change in waveguide characteristic as a result of absorbing chemical vapors. Bowman et al. use two gratings (diffraction gratings) embedded in a substrate for coupling incident and decoupling light. Such a grating coupler, however, is difficult to fabricate and expensive. A similar method using a simpler prism coupler has been reported by Osterfeld et al. in "Optical gas detection using metal film enhanced leaky mode spectroscopy" (Appl. Phys. Lett. 62 (19), 1993, pp 2310–2312). A metal reflective layer is sandwiched between a polymer film waveguide and an optical coupling prism such that light incident to the interface between the metal reflective layer and the prism is totally reflected at an optimal incident angle. Evanescent waves produced by total reflection excite a waveguide mode in the polymer film.

Reference has not been made as to whether or not the polymer waveguides proposed by Bowman et al. and Osterfeld et al. can be used for detecting organic carbon in water. Further, since the polymer film (teflon AF) used by Osterfeld et al. nas a refractive index (=1.3034) smaller than the refractive index (=1.33) of water, the film made of teflon AF does not function as a waveguide in water.

Optical sensors without using evanescent waves or guided waves have also been reported. For example, Gauglitz et al. have reported a method of reflection spectroscopy for detecting organic vapors using the swelling of polymer films (GIT Fachz. Lab., 889, 7/1990). In this method, a sensitive polymer thin film coated on a transparent substrate is irradiated with white light at a normal incidence from the substrate side, and reflected light from the polymer thin film is collected and analyzed by a spectrometer. Here, wavelength shift in the reflection spectra caused by polymer-vapor interaction is measured as an indication of organic vapor concentration. As will be later described, the normal incident arrangement is less sensitive and must therefore rely on spectral interferometry. In other words, the method of Gauglitz et al. is complicated and requires expensive and large equipment for implementation.

The present invention has been made to solve the foregoing problems of the known techniques, and its object is to provide an optical sensor for detecting a chemical substance dissolved or dispersed in water, particularly DOC, which is simple in structure, highly sensitive, and easy to fabricate.

To achieve the above object, the present invention provides an optical sensor for directly detecting a chemical substance dissolved or dispersed in water comprising:

at least one detecting element having a polymer thin film capable of interacting with the chemical substance;

at least one light source unit for emitting light for irradiating the polymer thin film; and a first photo-detector for detecting the intensity of light reflected from the polymer thin film.

In the present invention, while the polymer thin film is capable of detecting any chemical substance which is absorbed or adsorbed thereby, the polymer thin film is preferably used to detect organic carbon in terms of the sensitivity and so on.

The detecting element, the light source unit, and the photo-detector are integrally supported by a housing. The polymer thin film provided in the detecting element is preferably formed on a planar substrate. In one embodiment of the present invention, the polymer thin film is formed on a highly reflective substrate such as that made of silicon, metal or the like, and interaction between the polymer thin film and the organic carbon in water is detected in accordance with an IER method (so called the front-side IER, abbreviated as FS-IER). In another embodiment of the present invention, the polymer thin film is formed on an optically transparent substrate, with a light source and a photodetector being located on the substrate side, i.e., facing the side of the substrate on which the polymer thin film is not formed, and interaction between the polymer thin film and the organic carbon in water is detected in accordance with the IER method (so called the back-side IER, abbreviated as BS-IER). In another embodiment of the present invention, the polymer thin film is formed on a highly reflective metal layer deposited on a transparent substrate. The highly reflective metal layer has a thickness equal to or less than a wavelength of light from the light source unit, and is made of a material selected from a group including silver, gold, chrome, silicon, and germanium. In this embodiment, interaction between the polymer thin film and organic carbon in water is detected in accordance with one of a SPR method and a WG method.

The polymer thin film preferably has a thickness of 10 $\mu$m or less, more preferably 5 $\mu$m or less, and further preferably 3 $\mu$m or less. Desirably, the light source unit comprises a laser diode (LD) or a light emitting diode (LED), and the photo-detector is a photodiode or a phototransistor. An output of the photo-detector is applied to an electric circuit which generates a signal indicative of the concentration of a chemical substance in water.

In the present invention, the polymer thin film absorbs or adsorbs a chemical substance in water to directly respond to the chemical substance. As a result of such interaction, the polymer thin film exhibits a change in thickness and/or refractive index. Since such a physical change is related to the concentration of the chemical substance, the physical change can be measured in accordance with an optical approach such as an IER method, SPR method, waveguide mode method, or the like to derive the concentration of the chemical substance in water.

In the four optical methods, the concentration of the chemical substance in water may be measured as a function of the intensity of reflected light at a fixed detection angle. With the waveguide mode method, the concentration of the chemical substance is measured as a function of the reflectivity of the polymer thin film or an angular position of a waveguide mode.

In the FS-IER method, a light source and a photodetector are located above the polymer thin film such that probe light from the light source and reflected light from the polymer thin film pass through water in which organic substances are dissolved. This method is not always desirable because bubbles and particles in water may scatter or block light beams, causing large fluctuations or attenuation of output signal.

The BS-IER method takes an approach similar to that reported by Gauglitz et al., which employs a sensing element having a polymer thin film formed on an optically transparent substrate, with a light source and a photodetector being located on the substrate side, i.e., facing the side of the substrate on which the polymer thin film is not formed. The inventors of this invention, however, have found that when probe light is incident at an angle less than but close to the critical angle of total internal reflection, the reflectivity of the polymer thin film largely varies as compared with light incident normal to the polymer thin film, as reported by Gauglitz et al. This invention has been made based on this discovery and provides an optical sensor different from conventional evanescent wave sensors and guided wave sensors.

In the BS-IER method, the substrate couples light from the light source unit to the polymer thin film at a predetermined angle, and functions as light coupling means for coupling light reflected by the sensing element to the first light detector, and the predetermined incident angle is set at a value smaller than a critical angle of total internal reflection on the interface between the polymer thin film and the water and close to the critical angle.

In one embodiment of this invention, the optical sensor further comprises a second light detector for directly receiving light from the light source unit, and an electronic circuit to receive outputs of the first light detector and the second light detector for calculating the ratio of these outputs to generate a signal indicative of the concentration of the organic substance. The light source unit, the first light detector, the second light detector, and the light coupling means are mounted in a housing in a predetermined positional relationship with respect to the sensing element.

Also, the substrate may be a prism or a planar plate. When the substrate is a planar plate, a grating may be formed on a predetermined position of the substrate, or a grating layer formed with a grating may be disposed between the substrate and the polymer thin film or on a surface of the substrate on which the polymer thin film is not formed.

FIG. 1A generally illustrates the FS-IER structure of a first embodiment of an optical sensor according to the present invention;

FIGS. 8A–8D illustrate sensing elements utilizing grating coupling, and FIG. 8E illustrates a sensing element utilizing side-coupling;

Figure 9A:
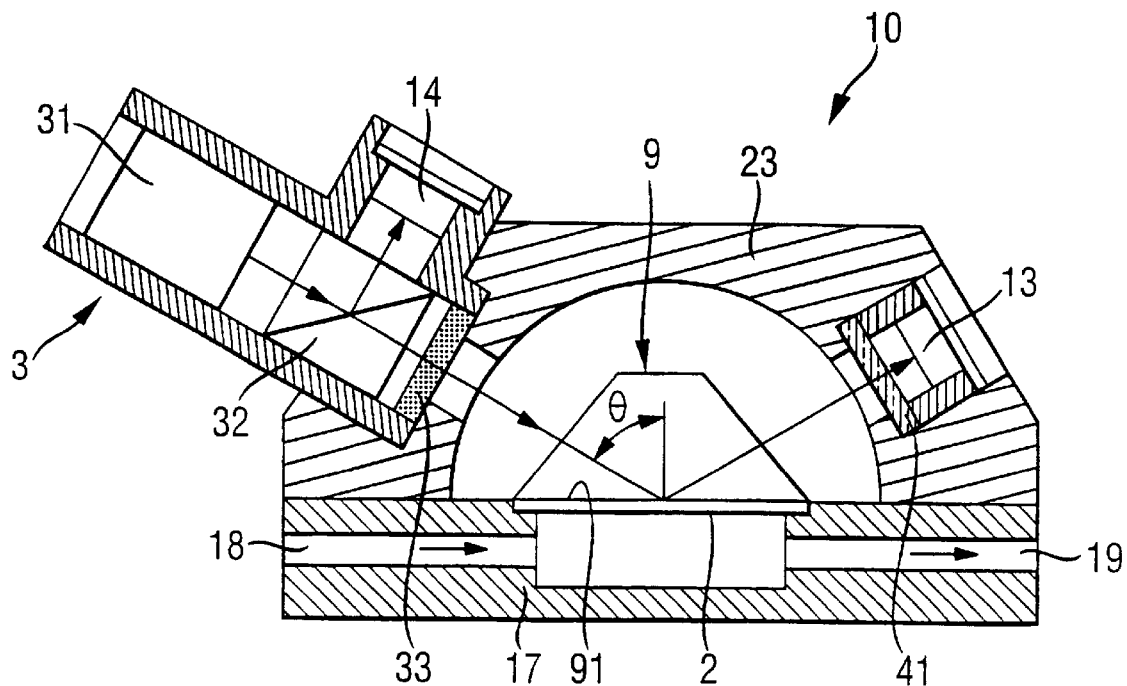
Figure 9B:
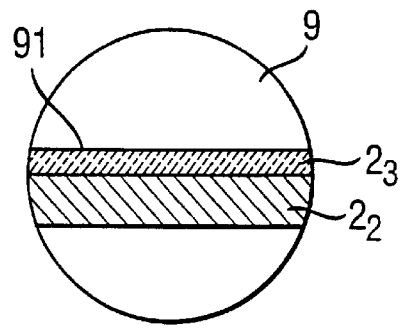
Figure 10:
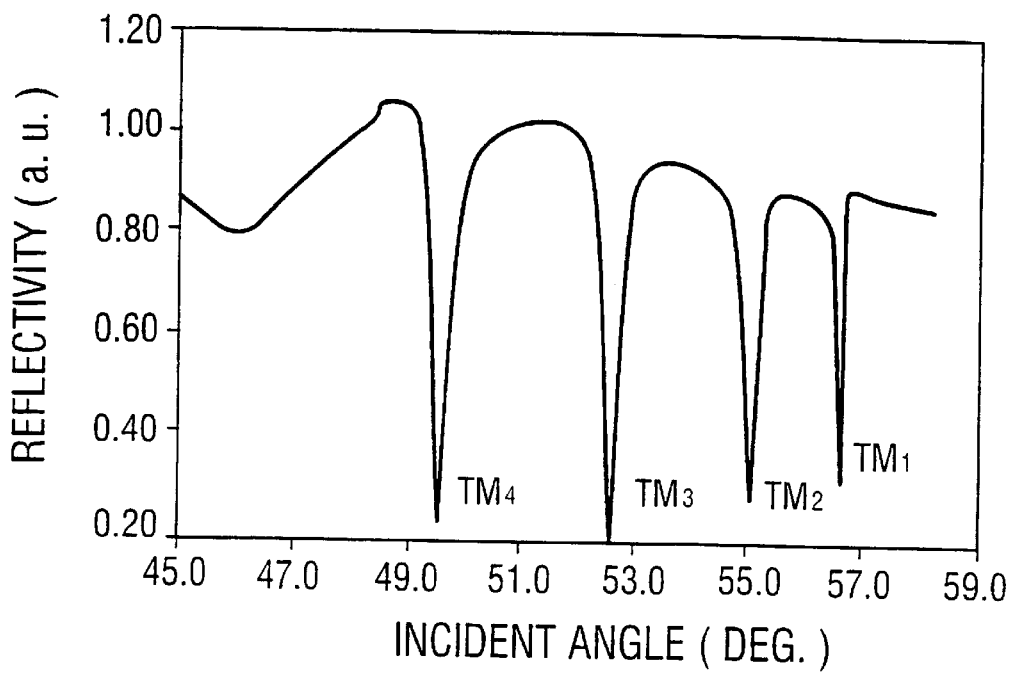
Figure 11:
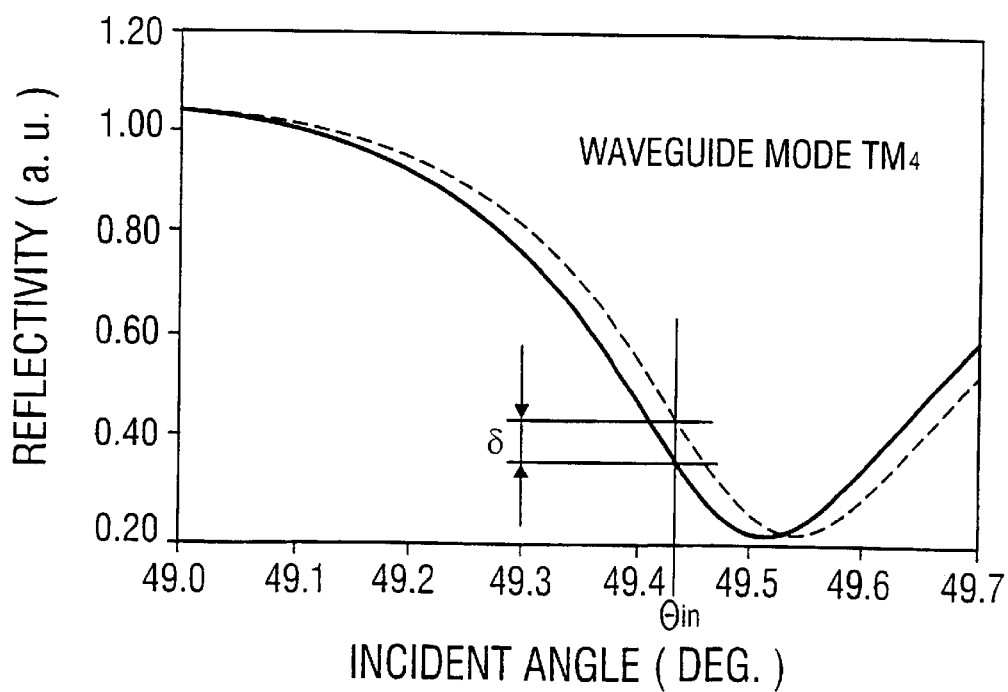
Figure 12:
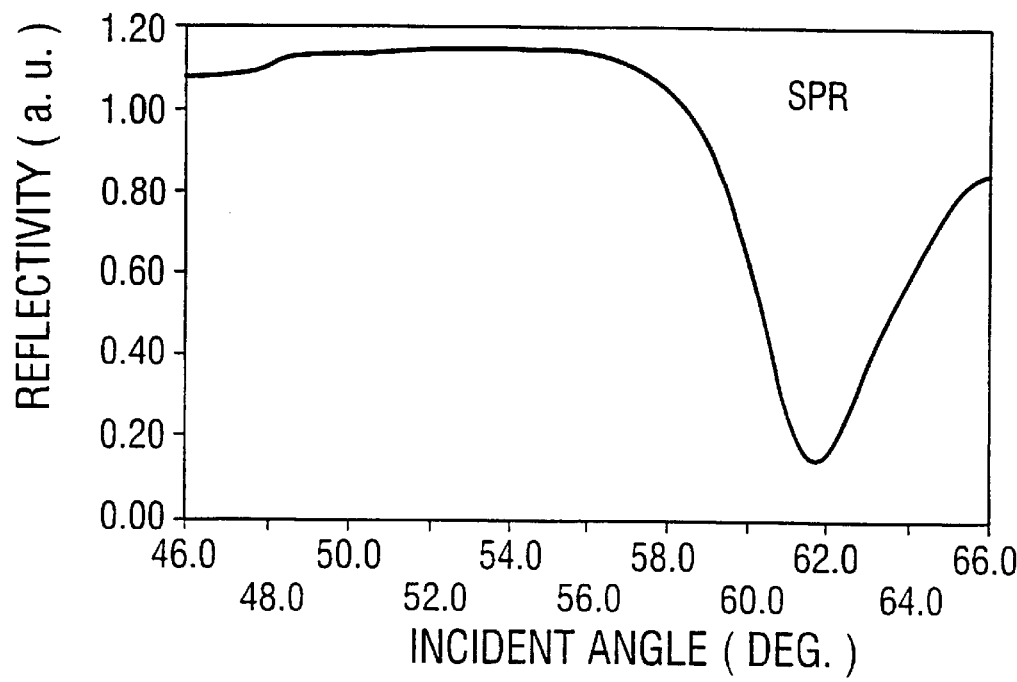
Figure 13:
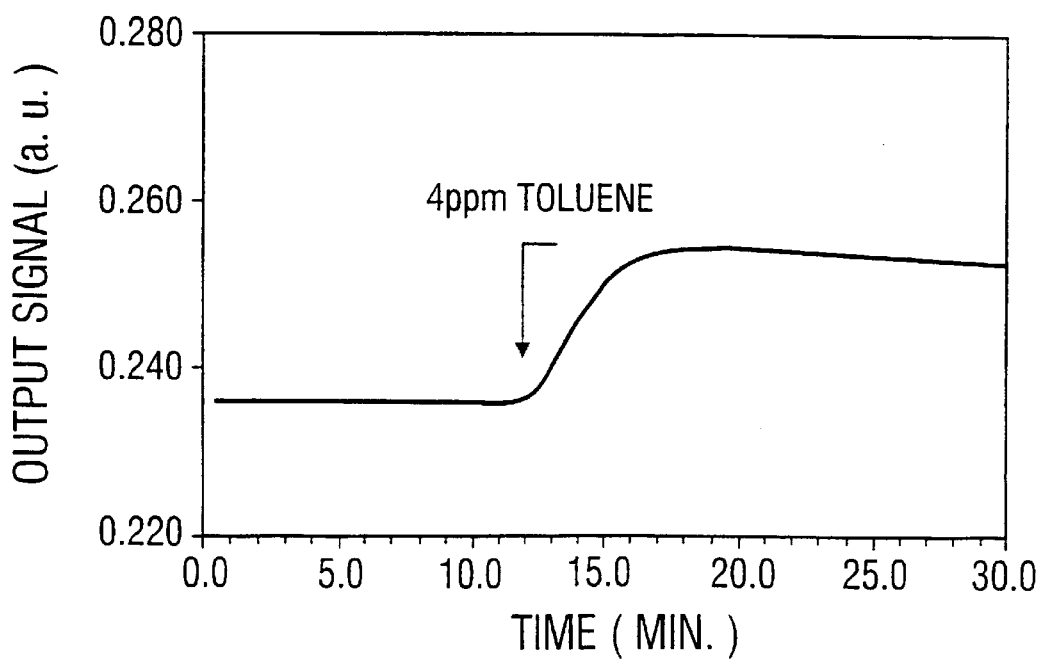
Figure 14:
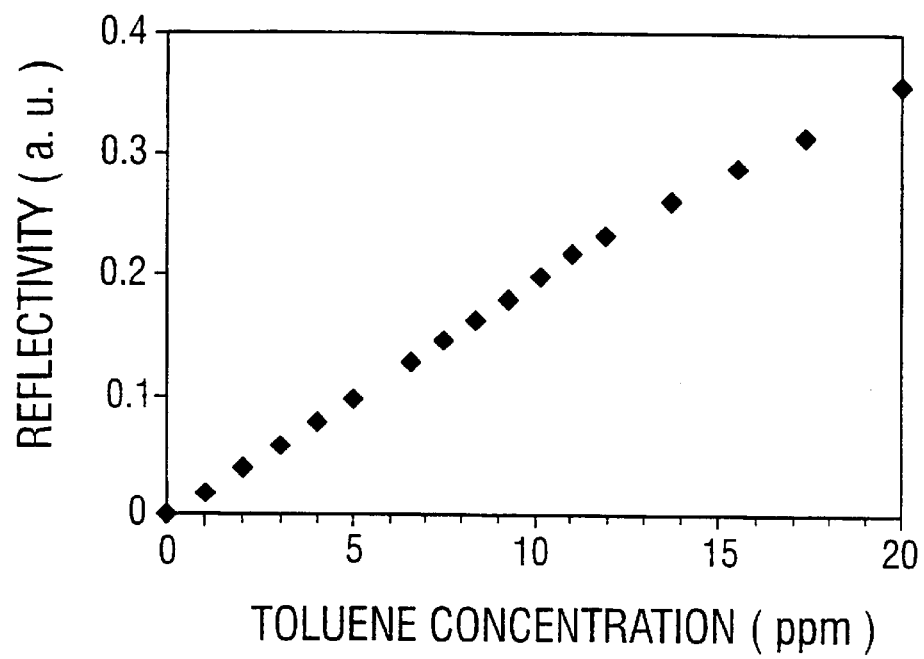
Figure 15:
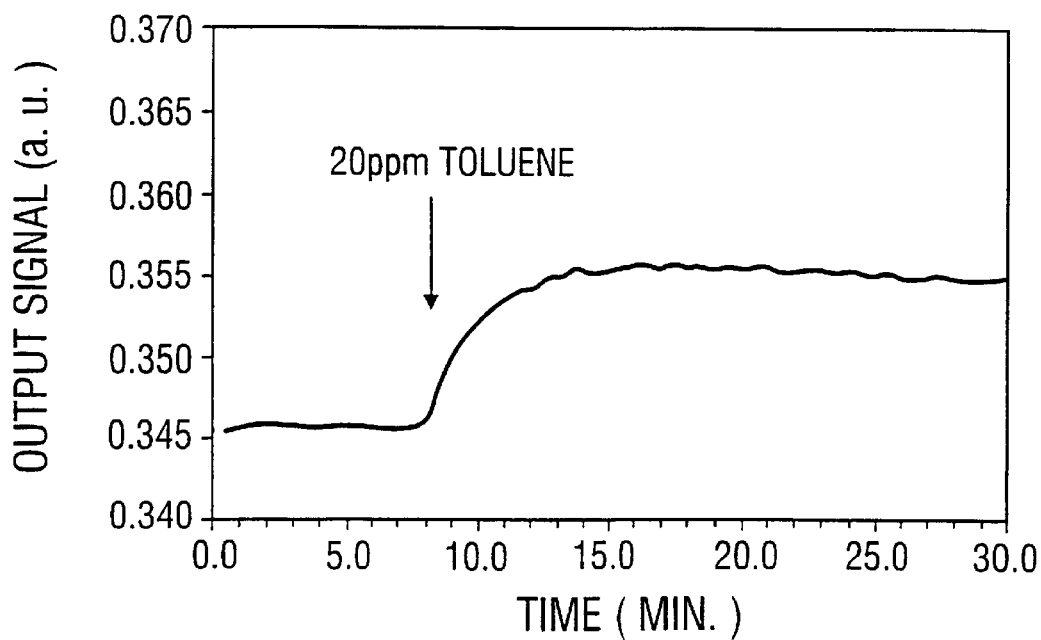
Figure 16:
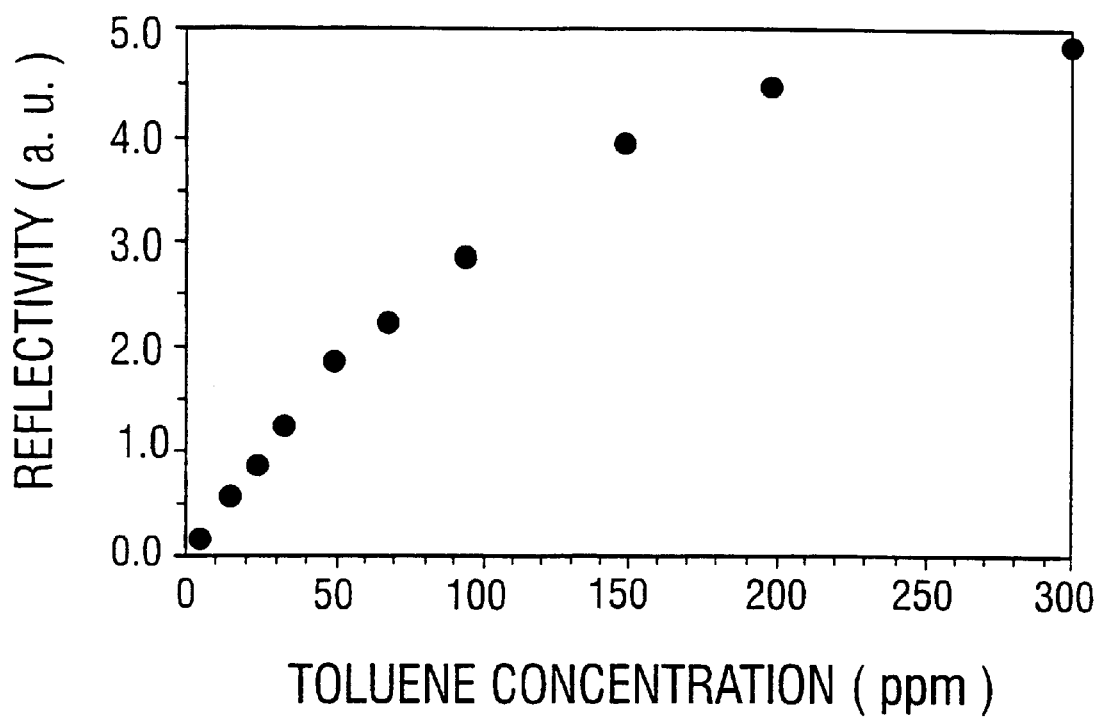

FIG. 9A generally illustrates the structure of a second embodiment of the optical sensor according to the present invention;

FIG. 9B is an enlarged cross-sectional view illustrating the structure of a detecting element in FIG. 9A;

FIG. 10 is a graph representing the relationship between an incident angle of light emitting on the polymer thin film in the optical sensor of FIG. 9A and the reflectivity of the polymer thin film;

FIG. 11 is a graph representing the relationship between an incident angle of light emitting on the polymer thin film in the optical sensor of FIG. 9A and the reflectivity of the polymer thin film when the polymer thin film is forced to respond to 2-ppm toluene, for showing a shift of a resonance coupling angle of a waveguide mode $TM_4$;

FIG. 12 is a graph representing the relationship between an incident angle of light and the reflectivity of the polymer thin film derived for a specific example of the optical sensor illustrated in FIG. 9A;

FIG. 13 is a graph showing how a response of an optical sensor having the same structure as the optical sensor of FIG. 9A varies over time for 4-ppm toluene in water;

FIG. 14 is a graph showing how a response of an optical sensor having the same structure as the optical sensor of FIG. 9A varies for a varying concentration of toluene in water;

FIG. 15 is a graph showing how a response of an optical sensor having the same structure as the optical sensor of FIG. 9A varies over time for 20-ppm toluene in water; and FIG. 16 is a graph showing how the reflectivity of a polymer thin film used in an optical sensor having the same structure as the optical sensor of FIG. 1 changes in response as the concentration of toluene in water varies.

Figure 17:
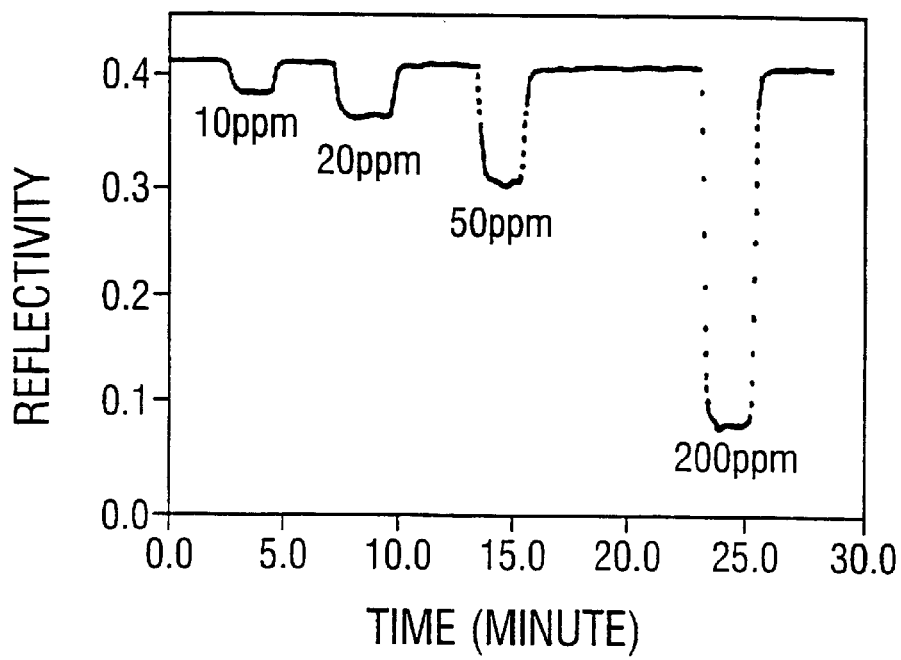
Figure 18:
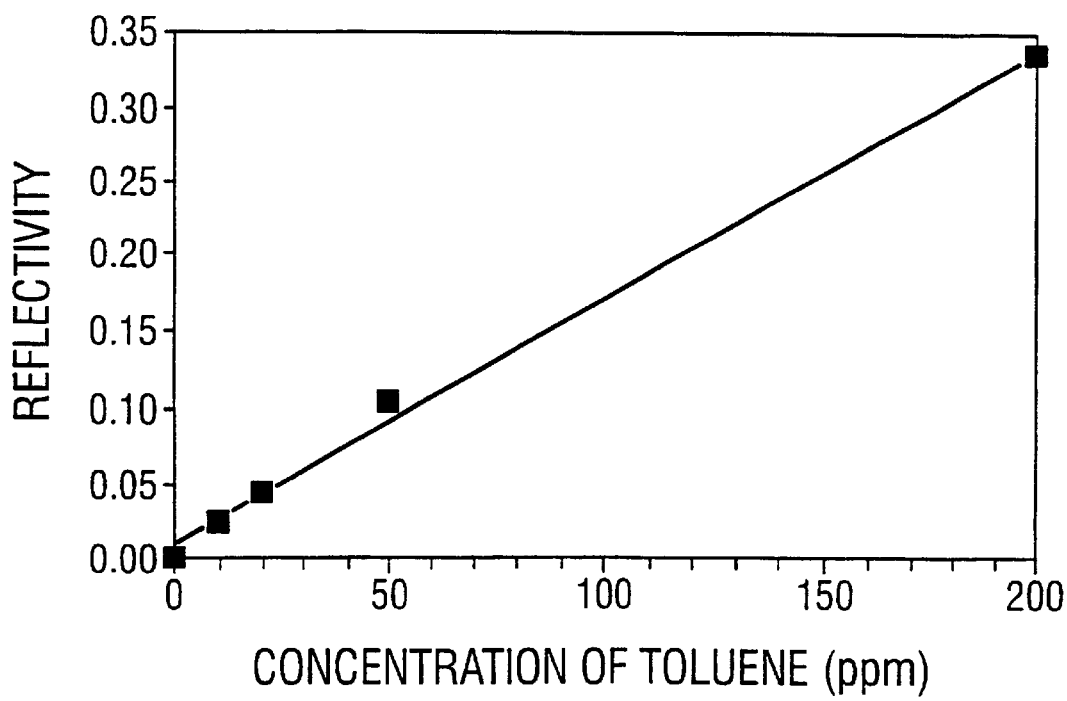
Figure 19:
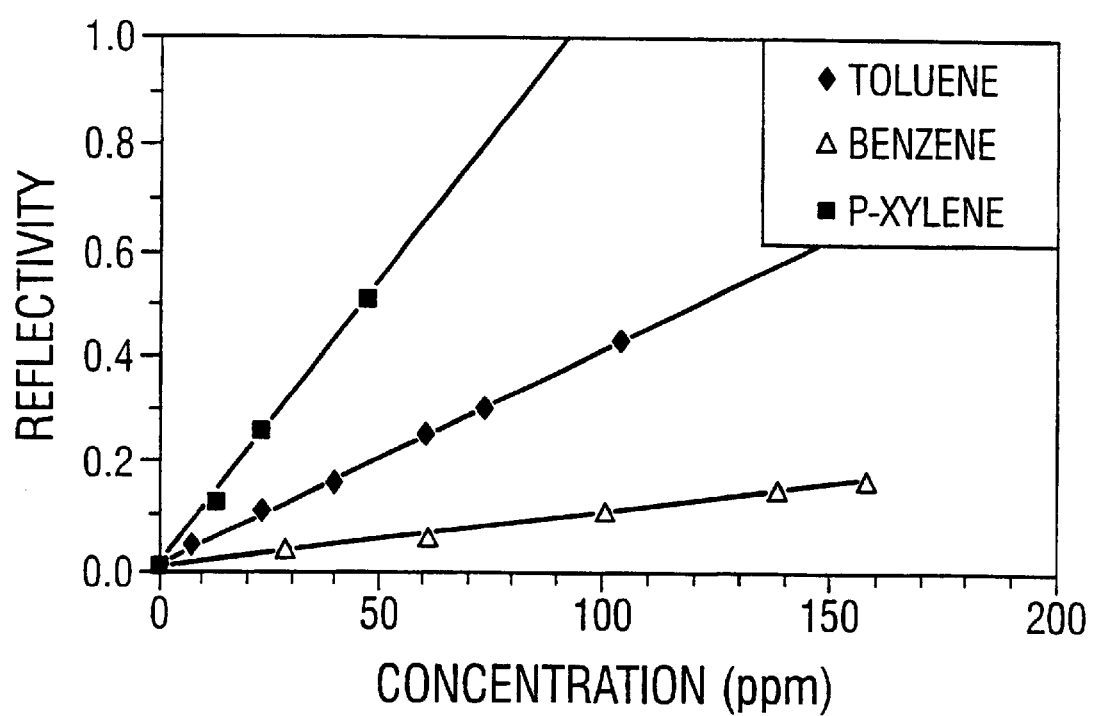

FIG. 17 is a graph illustrating a change in response time of the optical sensor according to this invention as a function of time when an organic substance in water is toluene having a concentration of 10–200 ppm;

FIG. 18 is a graph illustrating that the response of the optical sensor according to this invention linearly changes as the concentration of toluene in water varies; and FIG. 19 is a graph illustrating that the response of the optical sensor according to this invention linearly changes as the concentrations of toluene, benzene, and p-xylene in water vary.

A certain kind of polymer thin film (later described) exhibits a change in thickness and/or refractive index when a chemical substance such as organic carbon or the like is absorbed into or adsorbed on the polymer thin film. The present invention measures such a physical change of the polymer thin film to sense a chemical substance in water. Several embodiments of an optical sensor according to the present invention will hereinafter be described with reference to the accompanying drawings. It should be noted that in the drawings, the same or similar components are designated by the same reference numerals, and repetitive explanation thereof will be omitted.

Figure 1A:
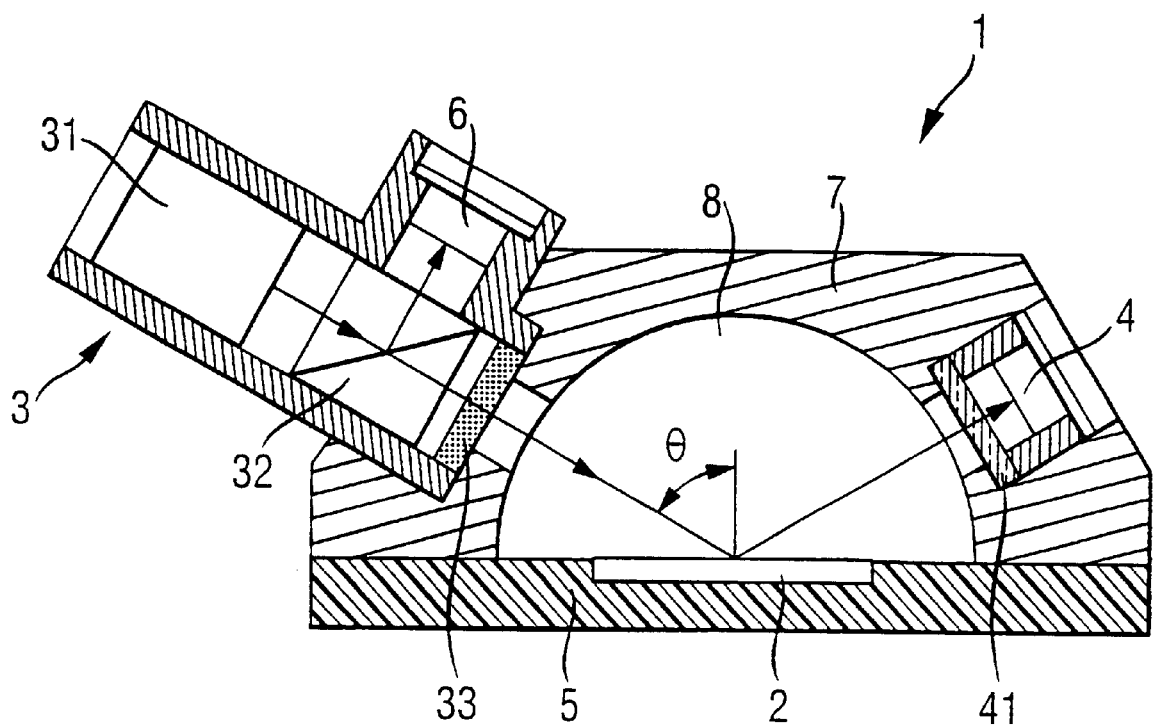
FIG. 1B is an enlarged cross-sectional view illustrating the structure of a detecting element in FIG. 1A.
Figure 1B:
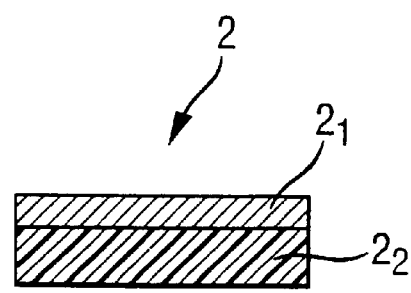

FIG. 1A generally illustrates the configuration of a first embodiment of an optical sensor according to the present invention, and FIG. 1B illustrates in an enlarged view a detector element used in the optical sensor. The sensor of the first embodiment relies on the FS-IER method for detecting a chemical substance in water. Referring specifically to FIG. 1A, the optical sensor 1 comprises the detecting element 2; a light source unit 3 for emitting light such that the light is incident to the detector element 2 at an incident angle θ; and a first photo-detector 4 for detecting the intensity of light emitted from the light source unit 3 and reflected by a polymer thin film $2_2$ of the detecting element 2.

The detecting element 2 is positioned on one surface of a base 5, and has a planar reflective substrate $2_1$ and the polymer thin film $2_2$ formed on the substrate $2_1$ in contact with water, as illustrated in FIG. 1B. The reflective substrate $2_1$ is preferably a substrate having a high reflectivity and may be, for example, mirror, semiconductor, metal, or a thin film of any metal material or any semiconductor material deposited on a low reflective substrate.

The light source unit 3 has a light source 31, a beam splitter 32, and a polarizing plate 33. The light source 31 may be a laser diode (LD) or a light emitting diode (LED) for emitting visual light or infrared rays. Light emitted from the light source 31 is split by the beam splitter 32 into two portions, one of which is polarized by the polarizing plate 33 and emits on the polymer thin film $2_2$ of the detecting element 2. Light reflected from the polymer thin film $2_2$ enters, through a window 41, the first photo-detector 4 which detects the intensity of received light. The other light portion split by the beam splitter 32 is directed to a second photo-detector 6 and transduced thereby into a signal representative of a reference light intensity.

The first photo-detector 4 and the second photo-detector 6 may be photodiodes or phototransistors. Outputs of these photo-detectors 4, 6 are transferred to an appropriate electronic circuit to calculate the ratio of the output of the first photo-detector 4 to the output of the second photo-detector 6. This ratio is used to generate a signal indicative of the concentration of a chemical substance to be detected.

The light source unit 3, the first photo-detector 4, and the second photo-detector 6 are mounted at appropriate locations in a housing 7. The housing 7 is mounted on the base 5 such that the housing 7 forms a water channel 8 with the base 5 and the polymer thin film $2_2$ of the detecting element 2 is in contact with water in the water channel 8. The light passing through the polarizing plate 33 is preferably s-polarized light which has an electric field vector of the light perpendicular to an incident plane of the polymer thin film $2_2$.

The IER method is utilized to detect a change in thickness and/or refractive index of the polymer thin film $2_2$ in contact with water based on the fact that the intensity of light reflected from a thin dielectric film depends on the thickness of the dielectric film. The polymer thin film $2_2$ exhibits a change in thickness and/or refractive index when it absorbs or adsorbs a chemical substance in water. Thus, when the polymer thin film $2_2$ is irradiated with light from the light source unit 3, a change in thickness and/or refractive index of the polymer thin film $2_2$ appears as a change in intensity of light reflected from the polymer thin film $2_2$. It is therefore possible to measure the concentration of a chemical substance in water by measuring the intensity of the reflected light.

Figure 2:
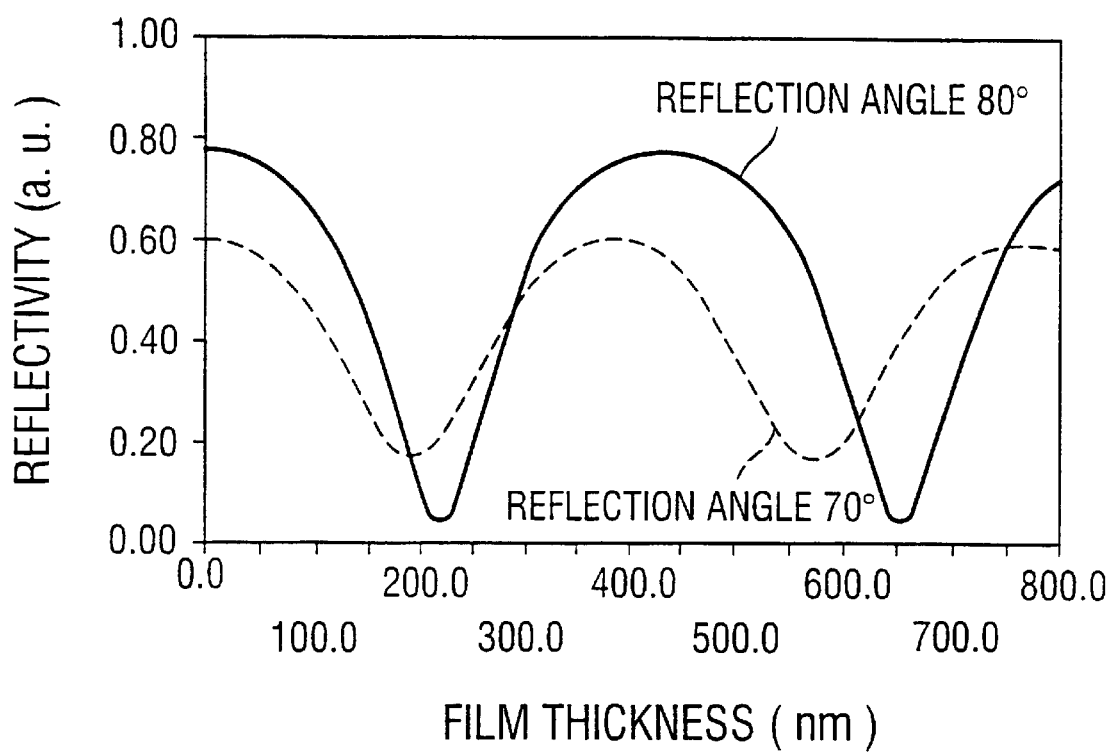
FIG. 2 is a graph representing the relationship between the thickness and the reflectivity of a polymer thin film in the optical sensor illustrated in FIG. 1A.

FIG. 2 illustrates a graph which represents the relationship between the thickness of the polymer thin film $2_2$ of the detecting element 2 in the optical sensor 1 shown in FIG. 1A and the reflectivity of the polymer thin film $2_2$ to s-polarized light incident thereto, when the polymer thin film $2_2$ is formed on a silicon substrate and placed in water. In other words, the graph shows reflectivity curves derived in accordance with the IER method. A solid line indicates the reflectivity when the incident angle θ of the light is 80, and a broken line indicates the reflectivity when the incident angle θ is 70. In this event, the refractive index of the polymer thin film is 1.50.

Although the thickness of the polymer thin film $2_2$ may be arbitrarily selected in a range of several nanometers (nm)–10 micrometers (μm), the thickness is desirably set at a value away from minimum values of the reflectivity curves in FIG. 2 in order to appropriately detect the thickness of the polymer thin film $2_2$ in accordance with the IER method. Also, it can be seen from the reflectivity curves of FIG. 2 that the reflectivity more largely modulates as the incident angle θ is larger (the reflectivity exhibits a larger change in response to a change in thickness). Thus, the incident angle θ is preferably 70 or more.

Figure 3:
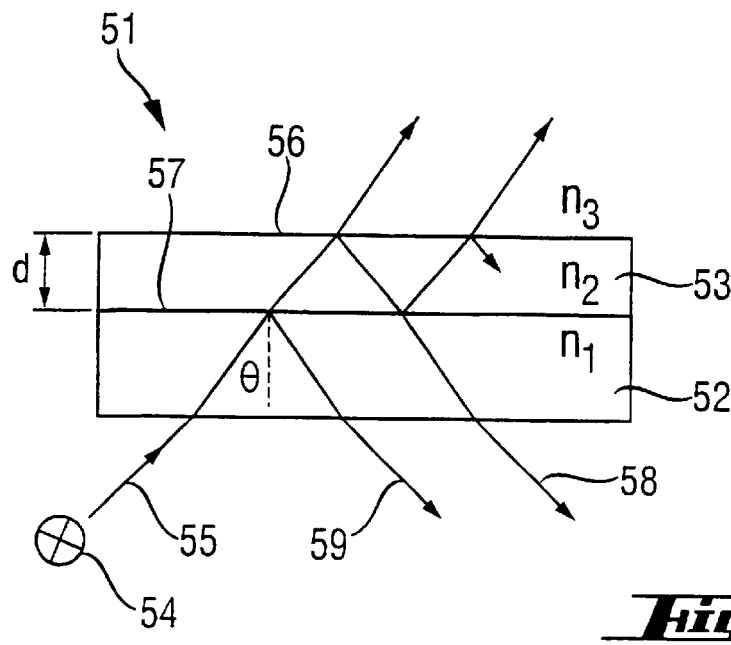
FIG. 3 is a schematic diagram illustrating a basic configuration of the BS-IER of a sensing element for use in an optical sensor according to this invention.

FIG. 3 generally illustrates a basic configuration of the BS-IER of a sensing element for use in the optical sensor according to this invention. Referring specifically to FIG. 3, a sensing element 51 comprises a transparent substrate 52 and a polymer thin film 53 formed on one surface of the substrate 52 by spin coating or the like. The polymer thin film 53 has a thickness $\underline{d}$ and a refractive index $n_2$. Other than the spin coating, the polymer thin film 53 may be formed by any of generally known methods such as vapor deposition, dip coating, roller coating, sputtering, chemical vapor deposition (CVD), and so on. Assume that the surface of the polymer thin film 53, opposite to the substrate 52, is in contact with water having a refractive index $n_3$. A light source 54 for emitting linearly polarized monochromic light of wavelength λ is located opposing the substrate 52. Monochromic light 55 emitted from the light source 54 is incident on the substrate 52 at an angle θ and reflected by an interface 56 between the polymer thin film 53 and the water and by an interface 57 between the polymer thin film 53 and the substrate 52, respectively. Thus, the intensity of reflected light from the sensing element 1 is a combination of the intensity of light 58 reflected by the interface 56 and the intensity of light 59 reflected by the interface 57, and therefore is the sum or difference of the intensities of the light 58, 59 depending on optical path lengths of the respective light 58, 59.

Figure 4:
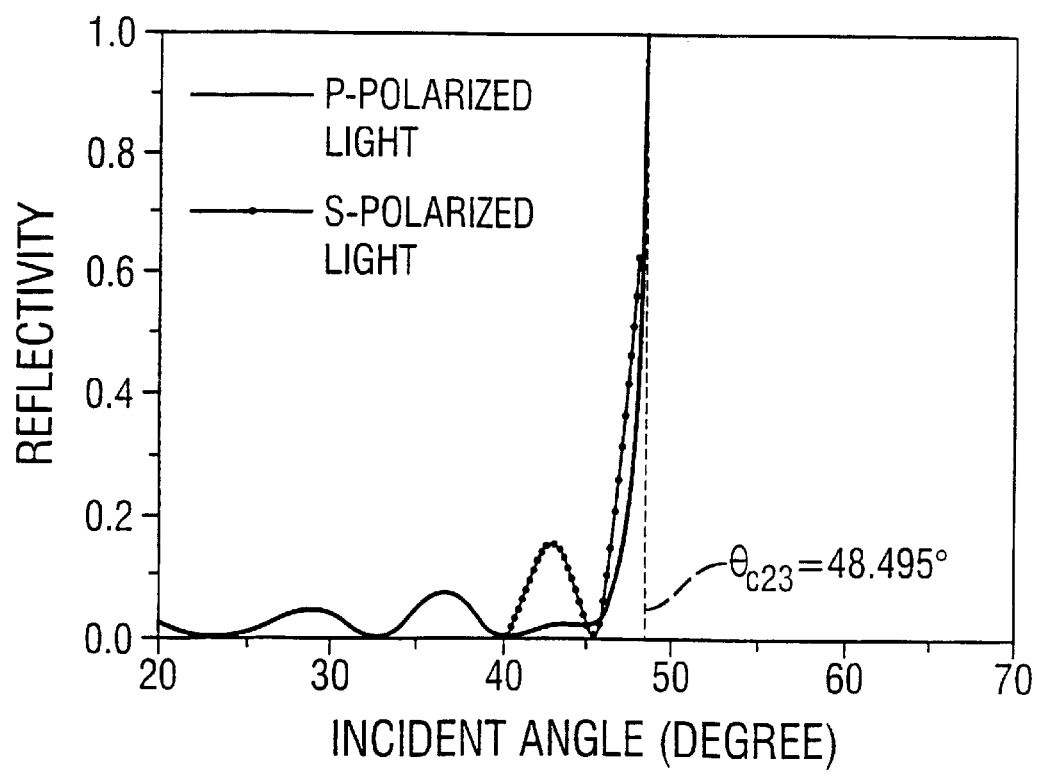
FIG. 4 is a graph illustrating the relationship between an incident angle of light and the reflectivity of a polymer thin film in the sensing element of FIG. 3.

The reflectivity of the sensing element 51 illustrated in FIG. 3 can be calculated using the well-Known Fresnel formula. As to further details on the Fresnel formula, see "Principles of Optics", by M Born and E. Wolf, Pergmon Press, 1959. Assume herein that a sensing element is formed of an SF11 glass substrate having a refractive index $n_1$ equal to 1.7786 and a poly(octadecyl methacrylate-co-glycidyl methacrylate) thin film (hereinafter referred to as "poly (ODMA-co-GLMA) thin film), having a thickness $\underline{d}$ equal to 1.8 μm and a refractive index $n_2$ equal to 1.493, coated on one surface of the glass substrate. The sensing element is located such that the poly(ODMA-co-GLMA) thin film is in contact with water having a refractive index $n_3$ equal to 1.332, with the exposed surface of the SF11 glass substrate irradiated with p-polarized light and s-polarized light of wavelength $\lambda$ equal to 632.8 nm. Then, the reflectivity of the poly(ODMA-co-GLMA) thin film is calculated in the measuring conditions mentioned above as a function of the incident angle of the light on the substrate. FIG. 4 illustrates the results of the calculations. As illustrated in the graph of FIG. 4, the critical angle of total internal reflection $\theta_{c23}$ is equal to 48.495° for the interface between the poly(ODMA-co-GLMA) thin film and the water. For reference, the critical angle of total internal reflection $\lambda_{c12}$ (not shown) is equal to 57.079° for the interface between the SF11 glass substrate and the poly(ODMA-co-GLMA) thin film.

It can be seen from the graph of FIG. 4 that when the incident angle $\theta$ of light is larger than the critical angle $\theta_{c23}$ (=48.495°), the reflectivity of the poly(ODMA-co-GLMA) thin film to the s-polarized light (TE wave) and the p-polarized light (TM wave) is unity, and does not at all depend on the thickness of the poly(ODMA-co-GLMA) thin film, and the reflectivity of the poly(ODMA-co-GLMA) thin film to the s-polarized light and the p-polarized light strongly depends on the thickness of the poly(ODMA-co-GLMA) thin film when the incident angle $\theta$ is smaller than the critical angle $\theta_{c23}$.

Figure 5:
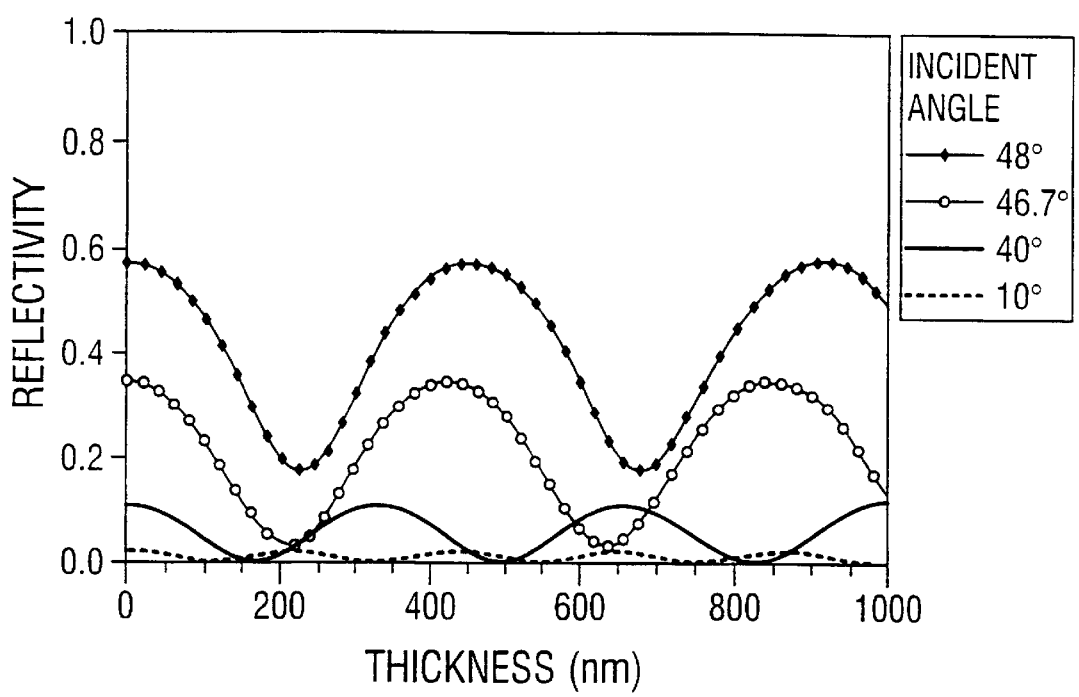
FIG. 5 is a graph illustrating the relationship between the thickness of a polymer thin film and its reflectivity in the sensing element of FIG. 3 for a plurality of incident angles.

FIG. 5 illustrates the relationship between the thickness of the poly(ODMA-co-GLMA) thin film and the reflectivity of the same to s-polarized light when the sensing element used for deriving the graph of FIG. 4 is irradiated with light of the same wavelength ($\lambda$=632.8 nm) for a plurality of incident angles smaller than the critical angle $\theta_{c23}$ (=48.495°). Comparison between reflectivity curves calculated with different incident angles illustrated in the graph of FIG. 5 reveals that the reflectivity of the poly(ODMA-co-GLMA) thin film strongly depends on its thickness as the incident angle $\theta$ approaches the critical angle $\theta_{c23}$ when the incident angle $\theta$ is smaller than the critical angle $\theta_{c23}$, and that the dependency of the reflectivity of the poly(ODMA-co-GLMA) thin film on its thickness is largest when the incident angle $\theta$ is around 48. The depth of modulation is abruptly reduced as the incident angle $\theta$ is smaller than the critical angle $\theta_{c23}$. At the incident angle $\theta$ equal to 10, the depth of modulation becomes extremely small.

It will be apparent from the above discussion that the normal incident arrangement used by Gauglitz et al., as described previously, has an extremely small change by the thickness or refractive index of a polymer thin film, and is therefore not sensitive. One embodiment of this invention is intended to provide an optical sensor which has a high sensitivity in a simple structure.

Figure 6A:
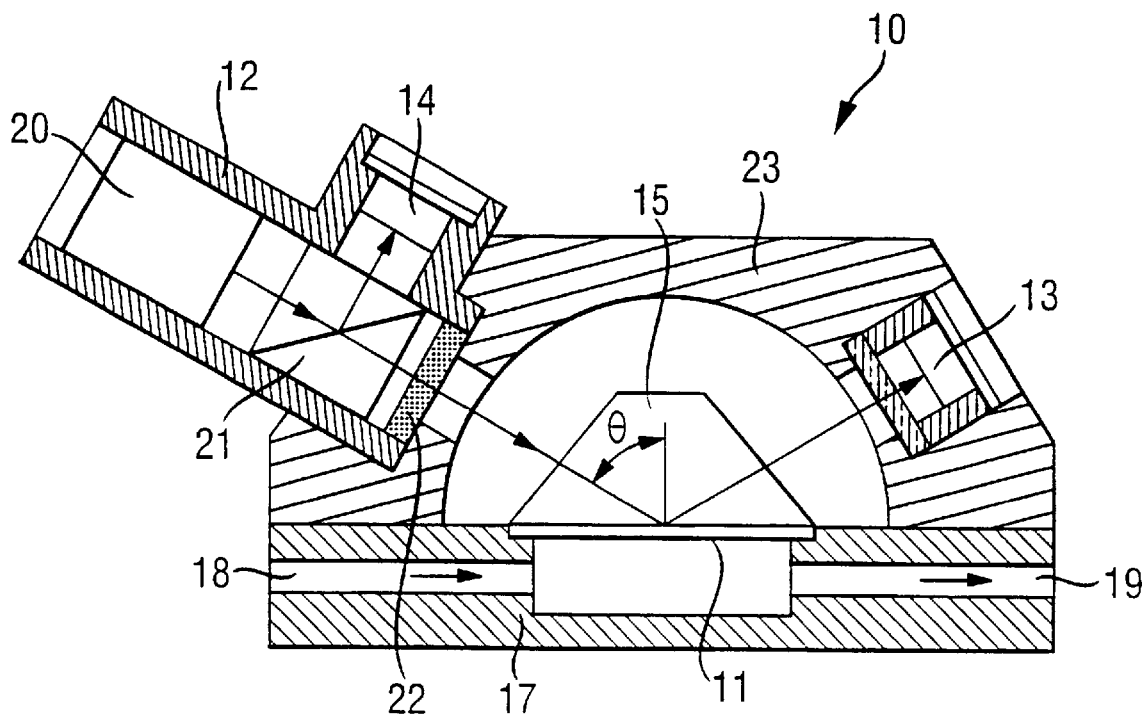
FIG. 6A is a cross-sectional view generally illustrating an embodiment of the optical sensor according to this invention.
Figure 6B:
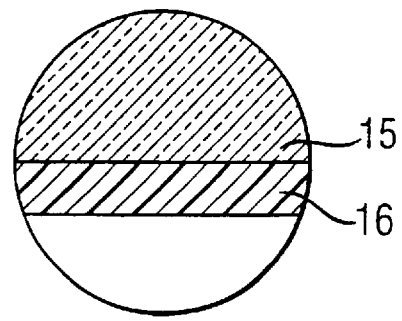
FIG. 6B is an enlarged view illustrating in detail a portion of the optical sensor of FIG. 6A.

FIG. 6A is a cross-sectional view generally illustrating the BS-IER configuration of an optical sensor according to the present invention. The optical sensor 10 comprises a sensing element 11, a light source unit 12, a first light detector 13, and a second light detector 14. As can be best seen in an enlarged view of FIG. 6B, the sensing element 11 comprises a polymer thin film 16 formed on one surface of a prism 15, acting as the substrate 2 of FIG. 3, in a predetermined thickness. The prism 15 is mounted on a flow cell 17 for passing water therethrough such that the polymer thin film 16 is in contact with water flowing through the flow cell 17. The flow cell 17 has a flow inlet 18 and a flow outlet 19 for water.

The light source unit 12 comprises a light source 20, a beam splitter 21, and a polarizing plate 22. The light source 20 may be, for example, a laser diode (LD) or a light emitting diode (LED) which emits visible light or infrared rays. Light emitted from the light source 20 is split by the beam splitter 21 into a probe beam and a reference beam. The probe beam passes through the polarizing plate 22 and becomes a linearly polarized beam. The polarization of this linearly polarized beam is preferably an S-polarization (i.e., the electric field of the light beam is oriented perpendicular to the plane of incident). The probe beam passes through the prism 15, is incident on the polymer thin film 16 at an incident angle $\theta$ smaller than a critical angle of total internal reflection $\theta$ on the interface between the polymer thin film 16 and water, and is reflected by the polymer thin film 16. The reflected probe beam is received by the first light detector 13 which transduces the probe beam into an electric signal indicative of the intensity of the reflected light. The reference beam, which is the other light beam split by the beam splitter 21, is received by the second light detector 14 which transduces the received light beam into an electric signal indicative of a light intensity for reference. The signals outputted from the first light detector 13 and the second light detector 14 are supplied to an appropriate electronic circuit having, for example, a sampling hold circuit, a comparator, and so on, for calculating the ratio between these signals. The concentration of an organic substance in water can be determined using this ratio.

For implementing the emission, reflection, and detection of light beams, the light source unit 12, the first light detector 13, and the second light detector 14 are mounted in a housing 23 in a predetermined positional relationship with respect to the sensing element 11 as illustrated in FIG. 6A. Alternatively, optical fibers may be used to couple between the light source 12 and the prism 15 and between the prism 15 and the first light detector 13. Photodiodes and phototransistors may be used as the first light detector 13 and the second light detector 14, by way of example.

In the optical sensor according to the BS-IER method, the incident angle $\theta$ of light emitted from the light source unit is desirably smaller than the critical angle of total internal reflection $\theta$ on the interface between the polymer thin film and water and close to the critical angle $\theta c$. By selecting the incident angle $\theta$ such that the reflectivity of the polymer thin film of zero thickness, is preferably 0.1 or more, particularly preferably 0.2 or more, and further preferably 0.3 or more, more highly sensitive sensors can be provided. For example, as illustrated in the graph of FIG. 5, s-polarized light having the wavelength at 632.8 nm is preferably incident at an incident angle $\theta$ ranging from 40° and 48° on a poly(ODMA-co-GLMA) thin film spin-coated on an SF11 glass substrate. On the other hand, while it is desirable that the thickness of a polymer thin film is generally in a range of several nanometers to 10 $\mu$m, the thickness of a polymer thin film optimal to the detection in accordance with the IER method is not limited in particular. However, as will be understood from the graph of FIG. 5, since a change in reflectivity is small near a maximum value or a minimum value of the reflectivity, the thickness of the polymer thin film is desirably selected in the middle of a thickness at which the reflectivity is maximum and a thickness at which the reflectivity is minimum.

Figure 7:
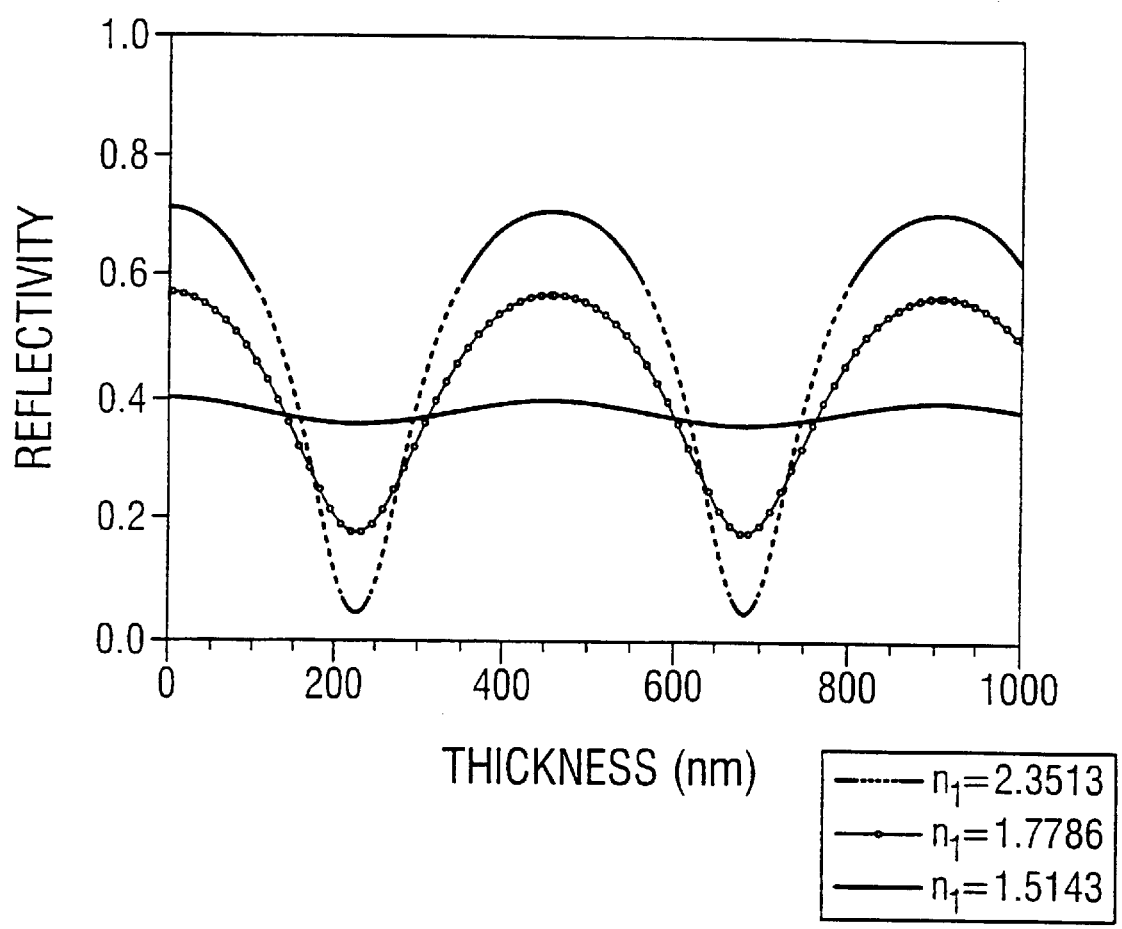
FIG. 7 is a graph illustrating the relationship between the thickness of a polymer thin film and its reflectivity in the optical sensor of FIG. 6 for a plurality of substrates having different refractive indices.

The substrate for use in the sensing element of the optical sensor according to the BS-IER method is preferably transparent and may be made of materials including, for example, glass, plastic, polymer and semiconductor. In addition, an extremely thin metal layer, inorganic dielectric film or semiconductor film (50 nm or less) may be vapor deposited on such a transparent substrate. It should be noted, however, that the reflectivity of a polymer thin film varies depending on the refractive index of a material used for the substrate. FIG. 7 is a graph showing how the refractive index of a substrate influences the reflectivity of a polymer thin film. For the purpose of measurements, three sensing elements are prepared. Specifically, a poly(ODMA-co-GLMA) thin film having a thickness d equal to 1.8 $\mu$m and a refractive index $n_2$ equal to 1.493 is formed by spin-coating on one surface of each of three transparent substrates having a refractive index n1equal to 1,5143, 1.7786 and 2.3513, reflectively. Each of the sensing elements is positioned such that the poly(ODMA-co-GLMA) thin film is in contact with water having a refractive index $n_3$ equal to 1.332. The graph shows the relationship between the thickness of the polymer thin film and its reflectivity when each substrate is irradiated with a light beam having a wavelength equal to 632.8 nm. It can be seen from the graph that a substrate having a larger refractive index allows the reflectivity of polymer thin film to be more sensitive to a change in its thickness, and accordingly is desirable for use in the optical sensor.

Continuing the explanation on the substrate, the prism 15 of the sensing element 11 in the optical sensor illustrated in FIG. 6A acts as a light coupling means for coupling the probe beam from the light source unit 12 to the polymer thin film 16 and for coupling a reflected beam therefrom to the first light detector 13 as well as constitutes the substrate 2 for forming the polymer thin film 16 thereon. However, such a light coupling means is not limited to the prism but may be realized by a variety of other means. Typical examples of such coupling means may be those utilizing grating coupling and side-coupling.

Figure 8A:
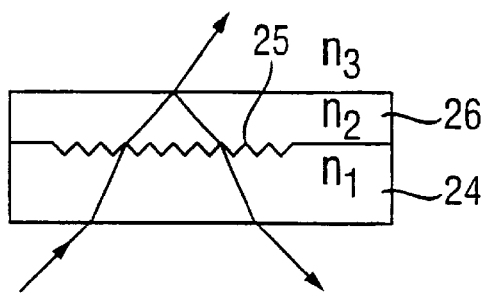
FIGS. 8A–8E are cross-sectional views for explaining exemplary modifications to the sensing element in the optical sensor according to this invention, where
Figure 8B:
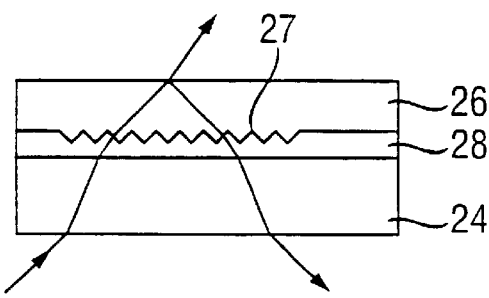
Figure 8C:
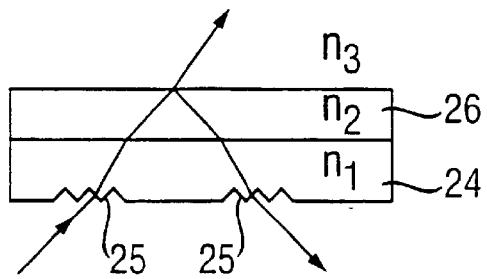
Figure 8D:
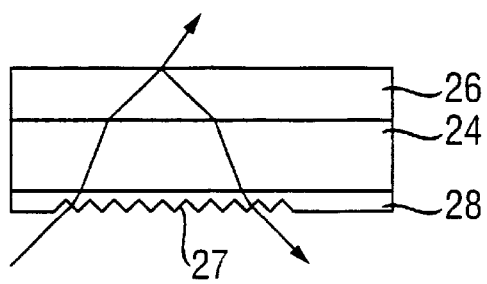
Figure 8E:
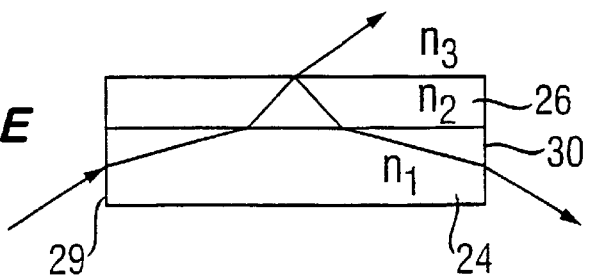

In the following, sensing elements utilizing the grating coupling will be described with reference to FIGS. 8A–8D, and a sensing element utilizing the side-coupling with reference to FIG. 8E. FIG. 8A illustrates a sensing element which has a grating 25 on a portion of a surface of a transparent substrate 24 and a polymer thin film 26 coated on the surface having the grating 25 formed thereon. A sensing element illustrated in FIG. 8B has a grating layer 28 formed with a grating 27 positioned between a substrate 24 and a polymer thin film 26. A sensing element illustrated in FIG. 8C is formed with a grating 25 on a surface of a substrate 24 in a portion on which light is incident and in a portion from which light reflected by a polymer thin film 26 exits. FIG. 8D illustrates a sensing element which employs a grating layer 28 formed with a grating 27 on a surface, on which light is incident, and mounted on a surface of a substrate 24 opposite to a polymer thin film 26. A sensing element illustrated in FIG. 8E, in turn, utilizes the side-coupling such that light is detected to be incident on one side surface 29 perpendicular to a polymer thin film 26 on a substrate 24 and reflected light from the polymer thin film 26 is led out through the other side surface 30.

FIG. 9A generally illustrates the configuration of a third embodiment of the optical sensor according to the present invention, and FIG. 9B is an enlarged cross-sectional view illustrating the structure of a detecting element shown in FIG. 9A. The third embodiment differs from the second embodiment of FIG. 6A in that the second embodiment uses a polymer waveguide formed on a metal cladding layer.

Referring specifically to FIGS. 9A and 9B, a metal layer $2_3$ is deposited on the bottom 91 of a prism 9, and a polymer thin film $2_2$ serving as a polymer waveguide is formed on the metal layer $2_3$ to complete a detecting element 2. The prism 9 is mounted on a flow cell 17 having a water flow inlet 18 and a water flow outlet 19 such that the polymer thin film $2_2$ faces water passing through the flow cell 17. Light emitted from a light source unit 3 and polarized by a polarizing plate 33 is incident to the bottom 91 of the prism 9 at an angle larger than an internal total reflection angle of the prism 9, and the intensity of light reflected by the bottom 91 is measured by a first photo-detector 4. The metal layer $2_3$ has a thickness equal to or less than the wavelength of the light emitted from a light source 31, and preferably made of silver, gold, chrome, silicon, or germanium.

When the light emitted from the light source 31 is totally reflected by the bottom 91 of the prism 9, evanescent waves are produced and light waves in a waveguide mode are excited by the evanescent waves. Such excitation of the waveguide mode in the polymer thin film $2_2$ i.e., optical coupling is the strongest at the incident angle at which a tangential component of an evanescent wave vector on the bottom 91 of the prism 9 is equal to a wave vector of the light waves in the waveguide mode. Thus, under such a condition, the energy of incident light from the light source 31 transitions to light waves in the waveguide mode internal to the polymer thin film $2_2$, whereby the intensity of light reflected from the metal layer $2_3$ is abruptly decreased.

Thus, when the reflectivity of the polymer thin film $2_2$ is measured while varying the incident angle θ of the light from the light source 31, excitation of light waves in the waveguide mode can be recognized as abrupt attenuation of a curve representing the reflectivity at a certain resonance coupling angle. FIG. 10 is a graph of values measured in an experiment for showing changes in reflectivity of the polymer thin film $2_2$ with respect to an incident angle θ of light emitting on the detecting element 2 comprising a poly (ODMA-co-GLMA) layer of 2 $\mu$m in thickness. In the curve illustrated in FIG. 10, four waveguide modes $TM_1$, $TM_2$, $TM_3$, $TM_4$ can be recognized. The poly(ODMA-co-GLMA) layer may be spin coated on the surface of a gold layer having a thickness of approximately 50 nm vapor-deposited on the bottom of a rectangular prism made of SF11 glass (the refractive index of which is 1.7780 at wavelength of 632.8 nm). Since the poly(ODMA-co-GLMA) layer has a refractive index of approximately 1.46 in water, which is larger than those of water and gold, the poly(ODMA-co-GLMA) layer functions as a waveguide.

When the polymer thin film $2_2$ responds to a chemical substance in water, i.e., absorbs or adsorbs the chemical substance, the polymer thin film $2_2$ exhibits a change in thickness and/or refractive index to cause a shift of a resonance coupling angle at which a certain waveguide mode is excited. Such a shift of angle is a function of the concentration of the chemical substance. Thus, the concentration of a chemical substance in water can be sensed by measuring a shift of the resonance coupling angle associated with a certain waveguide mode. FIG. 11 is a graph representing a shift of the resonance coupling angle associated with the waveguide mode $TM_4$ (FIG. 10) when the polymer thin film $2_2$ responds to toluene in concentration of 2 ppm, resulted in a change δ of reflectivity. Specifically, a solid line represents the relationship between an incident angle of light emitting on the polymer thin film $2_2$ and the reflectivity of the polymer thin film $2_2$ when the concentration of toluene is 0 ppm, while a broken line represents the relationship between the incident angle and the reflectivity after the polymer thin film $2_2$ has responded to toluene in concentration of 2 ppm.

Instead of measuring a shift of the resonance coupling angle, the concentration of a chemical substance in water can be sensed by fixing an incident angle θ of light from the light source 31 at one side of the waveguide mode resonance and measuring a change in intensity of light reflected from the detecting element 2. Since the resonance is quite sharp, even a very small shift of the resonance coupling angle appears as a large change in reflectivity.

For supporting at least one waveguide mode, the polymer thin film $2_2$ illustrated in FIG. 9A must have a sufficient thickness. For example, a cutoff thickness of the polymer thin film $2_2$ having a refractive index of 1.45 in water is approximately 284 nm in order for the polymer thin film $2_2$ to have a TE0 mode. When the thickness of the polymer thin film $2_2$ is equal to or less than the cutoff thickness, any waveguide mode cannot exist in the polymer thin film $2_2$. It is however possible to observe a different phenomenon referred to as "surface plasmon resonance" (hereinafter abbreviated as "SPR").

The surface plasmon is plasma oscillation of free electrons existing on the boundary of a metal. This plasma oscillation is affected by the refractive index of a substance proximate to a surface of a metal. For example, when p-polarized light is incident to the bottom 91 of the prism 9 in the optical sensor constructed as illustrated in FIG. 9A and evanescent waves are produced by internal total reflection, surface plasma oscillation can be excited. The plasma oscillation is excited at an incident angle θ at which a tangential component of an evanescent wave vector on the bottom 91 of the prism 9 matches a wave vector of plasma waves on an interface opposing to the polymer thin film $2_2$ (i.e., on the interface with the substrate) with respect to the metal layer $2_3$. In this event, the energy of the incident light is transferred to plasma waves to cause the intensity of reflected light to abruptly attenuate. This phenomenon is the surface plasmon resonance (SPR). The position of the resonance coupling angle of SPR largely depends on the refraction of the polymer thin film on the surface of the metal layer, so that the SPR method may also be unitized to sense a chemical substance in water.

When the reflectivity to total internal reflected light is measured while varying an incident angle θ of incident light, the SPR can be experimentally observed as abrupt attenuation of the reflectivity at a certain resonance coupling angle. As an example of observed SPR, FIG. 12 illustrates a reflectivity curve (SPR curve) showing how the reflectivity of the polymer thin film used in the optical sensor illustrated in FIG. 9A varies with respect to an incident angle 6 when the optical sensor comprises a poly(ODMA-co-GLMA) layer having a thickness of 107 nm which is spin coated on the surface of a gold layer having a thickness of 50 nm vapor-deposited on the bottom of a rectangular prism made of SF11 glass (the refractive index of which is 1.7780 at wavelength of 632.8 nm).

Another optical sensor having the structure illustrated in FIG. 9A and relying on the SPR method can also be realized. While this optical sensor is also irradiated with p-polarized light, the polymer thin film should be as thin as possible, and preferably has a thickness in a range between several nanometers and several hundreds of nanometers. This is because the surface plasmon is a surface phenomenon and is sensitive to a change which may occur at a position several nanometers to several hundreds of nanometers away from the surface of the metal layer. When the polymer thin film absorbs or adsorbs a chemical substance in water and swells to cause a change in thickness and/or refractive index, the resonance coupling angle of SPR is shifted. It is therefore possible to sense the concentration of the chemical substance in water by measuring a shift of the resonance coupling angle of SPR or by measuring a change in intensity of light reflected from the polymer thin film with an incident angle of light from the light source being fixed at the near resonance coupling angle of SPR.

Materials for the polymer thin film used in the optical sensor according to the present invention preferably include a homopolymer or copolymer having a recurring unit represented by the following chemical formula (I):

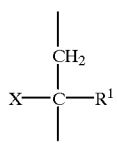

(I)

where X represents —H, —F, —Cl, —Br, —CH$_3$, —CF$_3$, —CN, or —CH$_2$—CH$_3$;

R$^1$ represents —R$^2$ or —Z —R$^2$;

Z represents ——, —S—, —NH—, —NR$^2$—, —(C=Y)—, —(C=Y)—Y—, —Y—(C=Y)—, —(SO$_2$)—, —Y'—(SO$_2$)—, —(SO$_2$)—Y'—, —Y'—(SO$_2$)—Y'—, —NH—(C=O)—, —(C=O)—, —(C=O)—NH—, —(C=O)—NR$^{2'}$—, —Y'—(C=Y)—Y'—, or —O—(C=O)—(CH$_2$)n—(C=O)—O—;

Y represents the same or different O or S;

Y' represents the same or different O or NH;

n represents an integer ranging from 0 to 20; and

R$^2$ and R$^{2'}$ represent the same or different hydrogen, a linear alkyl group, a branched alkyl group, a cycloalkyl group, an un-saturated hydrocarbon group, an aryl group, a saturated or un-saturated hetero ring, or substitutes thereof. It should be noted that R$^1$ does not represent hydrogen, a linear alkyl group, or a branched alkyl group.

In the formula, X is preferably H or CH$_3$; R$^1$ is preferably a substituted or non-substituted aryl group or —Z—R$^2$; Z is preferably —O—, —(C=O)—O—, or —O—(C=O)—; R$^2$ is preferably a linear alkyl group, a branched alkyl group, a cycloalkyl group, an un-saturated hydrocarbon group, an aryl group, a saturated or un-saturated hetero ring, or substitutes thereof.

A polymer used as the polymer thin film $2_2$ for the present invention may be a polymer consisting of a single recurring unit (I), a copolymer consisting of another recurring unit and the above-mentioned recurring unit (I), or a copolymer consisting of two or more species of the recurring unit (I). The recurring units in the copolymer may be arranged in any order, and a random copolymer, an alternate copolymer, a block copolymer or a graft copolymer may be used by way of example. Particularly, the polymer thin film is preferably made from polymethacrylic acid esters or polyacrylic acid esters. The side-chain group of the ester is preferably a linear or branched alkyl group, or a cycloalkyl group with the number of carbon molecules ranging preferably from 4 to 22.

Polymers particularly preferred for the polymer thin film are listed as follows:

poly(dodecyl methacrylate);
poly(isodecyl methacrylate);
poly(2-ethylhexyl methacrylate);
poly(2-ethylhexyl methacrylate-co-methyl methacrylate);
poly(2-ethylhexyl methacrylate-co-styrene);
poly(methyl methacrylate-co-2-ethylhexyl acrylate);
poly(methyl methacrylate-co-2-ethylhexyl methacrylate);
poly(isobutyl methacrylate-co-glycidyl methacrylate);
poly(cyclohexyl methacrylate);
poly(octadecyl methacrylate);
poly(octadecyl methacrylate-co-styrene);

poly(vinyl propionate);
poly(dodecyl methacrylate-co-styrene);
poly(dodecyl methacrylate-co-glycidyl methacrylate);
poly(butyl methacrylate);
poly(butyl methacrylate-co-methyl methacrylate);
poly(butyl methacrylate-co-glycidyl methacrylate);
poly(2-ethylhexyl methacrylate-co-glycidyl methacrylate);
poly(cyclohexyl methacrylate-co-glycidyl methacrylate);
poly(cyclohexyl methacrylate-co-methyl methacrylate);
poly(benzyl methacrylate-co-2-ethylhexyl methacrylate);
poly(2-ethylhexyl methacrylate-co-diacetoneacrylamide);
poly(2-ethylhexyl methacrylate-co-benzyl methacrylate-co-glycidyl methacrylate);
poly(2-ethylhexyl methacrylate-co-methyl methacrylate-co-glycidyl methacrylate);
poly(vinyl cinnamate) poly(butyl methacrylate-co-methacrylate);
poly(vinyl cinnamate-co-dodecyl methacrylate);
poly(tetrahydrofurfuryl methacrylate);
poly(hexadecyl methacrylate);
poly(2-ethylbutyl methacrylate);
poly(2-hydroxyethyl methacrylate);
poly(cyclohexyl methacrylate-co-isobutyl methacrylate);
poly(cyclohexyl methacrylate-co-2-ethylhexyl methacrylate);
poly(butyl methacrylate-co-2-ethylhexyl methacrylate);
poly(butyl methacrylate-co-isobutyl methacrylate);
poly(cyclohexyl methacrylate-co-butyl methacrylate);
poly(cyclohexyl methacrylate-co-dodecyl methacrylate);
poly(butyl methacrylate-co-ethyl methacrylate);
poly(butyl methacrylate-co-octadecyl methacrylate);
poly(butyl methacrylate-co-styrene);
poly(4-methyl styrene);
poly(cyclohexyl methacrylate-co-benzyl methacrylate);
poly(dodecyl methacrylate-co-benzyl methacrylate);
poly(octadecyl methacrylate-co-benzyl methacrylate);
poly(benzyl methacrylate-co-benzyl methacrylate);
poly(benzyl methacrylate-co-tetrahydrofurfuryl methacrylate);
poly(benzyl methacrylate-co-hexadecyl methacrylate);
poly(dodecyl methacrylate-co-methyl methacrylate);
poly(dodecyl methacrylate-co-ethyl methacrylate);
poly(2-ethylhexyl methacrylate-co-dodecyl methacrylate);
poly(2-ethylhexyl methacrylate-co-octadecyl methacrylate);
poly(2-ethylbutyl methacrylate-co-benzyl methacrylate);
poly(tetrahydrofurfuryl methacrylate-co-glycidyl methacrylate);
poly(styrene-co-octadecyl acrylate);
poly(octadecyl methacrylate-co-glycidyl methacrylate);
poly(4-methoxystyrene);
poly(2-ethylbutyl methacrylate-co-glycidyl methacrylate);
poly(styrene-co-tetrahydrofurfuryl methacrylate);
poly(2-ethylhexyl methacrylate-co-propyl methacrylate);
poly(octadecyl methacrylate-co-isopropyl methacrylate);
poly(3-methyl-4-hydroxystyrene-co-4-hydroxystyrene);
poly(styrene-co-2-ethylhexyl methacrylate-co-glycidyl methacrylate);

It should be noted that in the methacrylate ester polymers or copolymers listed above, acrylate may be substituted for methacrylate. The polymers may be crosslinked on their own, or they may be crosslinked by introducing a compound that has crosslinking reactive groups. Suitable crosslinking reactive groups include, for example, an amino group, a hydroxyl group, a carboxyl group, an epoxy group, a carbonyl group, an urethane group, and derivatives thereof. Other examples include maleic acid, fumaric acid, sorbic acid, itaconic acid, cinnamic acid, and derivatives thereof.

Materials having chemical structures capable of forming carbene or nitrene by irradiation of visible light, ultraviolet light, or high energy radiation may also be used as crosslinking agents. Since a film formed from crosslinking polymer is insoluble, the polymer forming the polymer thin film of the sensor may be crosslinked to increase the stability of the sensor. The crosslinking method is not particularly limited, and methods utilizing irradiation of light or radioactive rays may be used in addition to known crosslinking methods, for example, a heating method.

It should be noted that in the optical sensor according to this invention, the refractive index of the polymer thin film and swelling of the polymer thin film vary with temperature, so that the characteristics of the optical sensor are inevitably affected somewhat by ambient temperature. For this reason, temperature control techniques or temperature compensation techniques are required for highly accurate measurements. Specifically, such temperature control and temperature compensation may be implemented by appropriate techniques including: (1) arrangement of the optical sensor in a temperature controlled housing or control of the temperature of water flowing through the flow cell; (2) creation of a temperature compensating signal using a temperature sensitive element attached on the optical sensor; (3) utilization of a polymer more sensitive than the polymer thin film to temperature to create a reference signal for temperature correction; and so on.

Further, the optical sensor according to this invention may be modified to allow for measurements of the concentration of a mixture of organic substances (for example, hydrocarbons) dissolved in water. Such modifications may be realized by one or a combination of the following options:

(1) a method using a kind of polymer thin film which has a low or small response to a plurality of kinds of chemical substances in water;

(2) a method using a plurality of polymer thin films, each of which is selectively responsive to a different kind of chemical substance in water, wherein responses derived from these polymer thin films are combined to output a signal indicative of the concentration of a mixture composed of a plurality of chemical substances in water;

(3) a method using a plurality of polymer thin films, each of which exhibits a different response to the same or different chemical substance in water, wherein responses derived from these polymer thin films are combined to output a signal indicative of the concentration of a mixture composed of a plurality of chemical substances in water; and (4) a method using one or a plurality of the above-mentioned polymer thin films in combination of different optical approaches (for example, the IER method, surface plasmon resonance, guided wave mode spectroscopy), to generate a signal indicative of the concentration of a mixture composed of a plurality of chemical substances in water.

It should be noted however that a plurality of sensing elements, light source units, and/or light sensing elements may be required depending on particular implementations using one or a combination of the foregoing approaches.

Actually, the sensitivity and response time of the optical sensor according to this invention may vary depending on the kind of organic substance to be measured. Thus, in order to accurately measure the total amount of organic substances and the concentrations of individual organic substances or groups of organic substances in a variety of applications, a multi-channel configuration of optical sensors may be configured using the methods (1)–(4) mentioned above, in combination of known pattern recognition techniques (for example, matrix analysis, neural network analysis, and so on).

Several examples of the optical sensor according to the present invention will be described below.

EXAMPLE 1

FIG. 13 is a graph showing how a response of an optical sensor having the structure illustrated in FIG. 9A varies over time when the concentration of toluene in water is 4 ppm. An employed detecting element comprised a poly(ODMA-co-GLMA) layer of 2 $\mu$m in thickness which was spin coated on a gold layer of 50 nm in thickness deposited on the bottom of a rectangular prism made of SF11 glass. A laser diode emitting light at wavelength of 670 nm was used for a light source. Light from the laser diode was split into a reference beam and measuring beam. The reference beam was directed to a silicon photodiode for reference, while the measuring beam was passed through a polarizing plate and directed to the bottom of the rectangular prism as p-polarized light. An incident angle of the measuring beam was set at a smaller angle of resonance in the $TM_4$ waveguide mode illustrated in FIG. 11. When the intensity of the measuring beam reflected by the bottom of the prism was measured by a silicon photodiode for measurement, four waveguide modes were observed as illustrated in FIG. 10.

Outputs of the two photodiodes for reference and for measurement were supplied to an electronic divider to calculate the ratio of the output of the photodiode for measurement to the output of the photodiode for reference. The calculated ratio was supplied to an electric circuit to generate an output signal indicative of a response of the optical sensor. The result of the measurement revealed that for detecting toluene in water, a detection limit was lower than the concentration at 1 ppm and a 90% response time (a time required to reach a complete response) was within three minutes.

EXAMPLE 2

FIG. 14 shows how the response of the same optical sensor used in Example 1 varies as the concentration of toluene in water changes. It should be noted that the response from the optical sensor was measured in the form of a change in reflectivity with respect to a change in concentration of toluene. The measurement revealed that the optical sensor linearly responded to toluene in water in concentration ranging from 0 to 20 ppm.

EXAMPLE 3

FIG. 15 is a graph showing how an output signal of the same optical sensor used in Example 1 varies over time when the concentration of toluene in water is 20 ppm. The optical sensor used in this measurement employed a polymer thin film formed of a poly(ODMA-co-GLMA) layer of 107 nm in thickness and a helium-neon laser at wavelength of 632.8 nm for the light source. Surface plasmon resonance was observed as illustrated in FIG. 12 by the use of the polymer thin film of 107 nm in thickness.

An incident angle of a measuring beam, i.e., p-polarized light to the bottom of a prism was 60.82 which was rather a small incident angle in FIG. 12 illustrating the resonance coupling angle in the SPR method. As the output signal of the optical sensor was recorded as a function of time, the output signal increased in response to toluene in concentration of 20 ppm, and a 90% response time was approximately 3 minutes.

EXAMPLE 4

The optical sensor having the structure illustrated in FIG. 1A was used to measure toluene in concentration ranging from 0 to 300 ppm in water in accordance with the FS-IER method. A detecting element had a poly(ODMA-co-GLMA) layer of 1.95 $\mu$m in thickness spin-coated on a silicon substrate, and was mounted in a housing as illustrated in FIG. 1A. Water was introduced into the housing by suction. A laser diode for emitting light at wavelength of 670 nm was employed for a light source. Light from the laser diode was divided into a reference beam and a measuring beam. The measuring beam was passed through a polarizing plate to be linearly polarized s-polarized light which was incident to the polymer thin film at an incident angle of 80 through a glass window.

The intensity of the measuring beam reflected by the polymer thin film was measured by a silicon photodiode for measurement, while the intensity of the reference beam was measured by a silicon photodiode for reference. Outputs of these two silicon photodiodes were supplied to an electronic divider to calculate the ratio of the output of the silicon photodiode for reference to the output of the silicon photodiode for measurement. The calculated ratio was used to generate an output signal by an appropriate electric circuit. FIG. 16 illustrates the reflectivity measured by the optical sensor in Example 4 which is plotted as a function of the concentration of toluene in water. It can be seen from FIG. 16 that the response of the optical sensor is not linear in the range of 0–300 ppm.

EXAMPLE 5

The optical sensor used to obtain the measurement results has the same structure as the optical sensor illustrated in FIG. 6A. A sensing element comprises a poly(ODMA-GLMA) thin film spin-coated on an SF11 glass substrate in a thickness of 1 $\mu$m and a 90° glass prism mounted on a surface of the glass substrate, on which the poly(ODMA-GLMA) thin film is not formed, by a refractive index matching oil. A He-Ne laser with a wavelength of 632.8 nm is used as a light source, while photodiodes are used as first and second light detectors. As previously explained, a laser beam emitted from the light source is split by a beam splitter into a probe beam and a reference beam. The probe beam is transformed into s-polarized light by a polarizing plate and directed to be incident on the prism at an incident angle of 45°, and the probe beam reflected by the poly(ODMA-GLMA) thin film is supplied to the first light detector. The reference beam, in turn, is supplied directly to the second light detector. Signals representative of the intensities of the probe beam and the reference beam are generated by the first and second light detectors, respectively, and supplied to an electronic circuit for producing measurement results.

FIG. 17 is a graph representing the reflectivity of the optical sensor in response to 10–200 ppm toluene dissolved in water as a function of time. It can be seen from this graph that the optical sensor of this invention has a high sensitivity and a fast response. Detection limit could be around 1–2 ppm, and the 90% response time is less than 2 minutes.

The relationship between the response of the sensing element and the concentration of toluene in water is as illustrated in FIG. 18 which reveals that the reflectivity of the sensing element linearly changes in proportion to the concentration of toluene in water.

EXAMPLE 6

Next, for examining how the response of the sensing element is related to the concentration of another organic substance in water, the reflectivity of the sensing element is measured while changing the concentrations of benzene and p-xylene in addition to toluene. The results are shown in FIG. 19. The graph of FIG. 19 reveals that the response of the sensing element linearly changes in proportion to the concentrations of the three kinds of organic substances, i.e., toluene, benzene, and p-xylene, and the sensitivity of the sensing element to toluene and p-xylene are 3.5 and 9.25, respectively, when the sensitivity of the sensing element to benzene is assumed to be one.

EXAMPLE 7

It is desirable that a polymer thin film has response to as many kinds of chemical substances under detection, i.e., DOC as possible for detecting DOC in water. The optical sensor used in Example 1 having a poly(ODMA-co-GLMA) layer of 2 μm in thickness was used to measure a large number of different kinds of DOC in water. The results of the measurements are listed in the following table. In the table, "Sensitivity" is a value representing a change in reflectivity in percent, and "time" represents a 90% response time.

TABLE 1

| Organic compound | Concentration (ppm) | Sensitivity | Time (Minute) |
|---|---|---|---|
| toluene $C_7H_8$ | 2 | 41.72 | 6 |
| benzene $C_6H_6$ | 2 | 10.34 | 4 |
| chlorobenzene $C_6H_5Cl$ | 2 | 87.07 | 9 |
| nitrobenzene $C_6H_5NO_2$ | 2 | 23.28 | 1.5 |
| -xylene $C_8H_{10}$ | 2 | 126.86 | 15 |
| chloroform $CHCl_3$ | 2 | 8.71 | 3 |
| carbon tetrachloride $CCl_4$ | 2 | 21.55 | 11.5 |
| 1,2-dichloroethane $ClCH_2CH_2Cl$ | 2 | 6.03 | 1.5 |
| dichloromethane $CH_2Cl_2$ | 2 | 1.38 | 1 |
| diethyl ether $C_4H_{10}O$ | 100 | 11.21 | 1.5 |
| tetrahydrofuran $O(CH_2)_4$ | 100 | 9.48 | 1 |
| acetone $C_3H_6O$ | 500 | 8.62 | 1 |
| propanol $C_3H_8O$ | 500 | 6.03 | 1 |
| methanol $CH_4O$ | 500 | 0.00 |  |
| acetic acid $C_2H_4O_2$ | 500 | 3.45 | <1 |
| hydrochloric acid HCl | 2000 | 25 | <1 |
| sulfuric acid $H_2SO_4$ | 2000 | 6.67 | <1 |

It can be seen from Table 1 that the sensitivity and response time of the optical sensor vary depending on the kind of DOC to be detected. A multi-channel system comprising an array of detecting elements or an array of polymer thin films is therefore necessary to detect a large number of DOC in variety of industrial applications and environment protecting applications. In addition, known pattern recognition techniques such as matrix analysis, neural network analysis, or the like may be applied together with such a multi-channel system in order to accurately determine a total amount of DOC, the concentration of each DOC, or the concentrations of a DOC group.

The pattern recognition techniques applicable to the detection of chemical substances in water using the optical sensor of the present invention are described in an article entitled "Detection of Hazardous Vapors Including Mixtures Using Pattern Recognition Analysis of Responses from Surface Acoustic Wave Device" by Susan L. Rosepehrsson et al. published in "Anal. Chem.", 1088, 60, pp 2801–2811; an article entitled "Development of Odorant Sensor Using SAW Response Oscillator Incorporating Odorant-Sensitive LB Films and Neural-Network Pattern Recognition Scheme" by Sang-Mok Chang et al, published in "Sensors and Materials", Vol. 1 (1995), pp 013–022; an article entitled "Polymer-based sensor arrays and multicomponent analysis for the detection of hazardous organic vapors in the environment" by Andreas Hierlemann et al. published in "Sensors and Actuators B" 26–27 (1995), pp 126–134; and so on.

As will be apparent from several embodiments and examples of the present invention described above in detail, the optical sensor according to the present invention is advantageous over the optical fiber sensor in that it directly detects a change in thickness and/or refractive index of a polymer thin film resulting from interaction with a chemical substance in accordance with an optical approach such as the IER method, WG method, SPR method, or the like, so that even a trace of change in thickness and/or refractive index can be detected with a high sensitivity. In addition, since the polymer thin film can be readily formed by an ordinary method such as spin coating, the optical sensor itself can be readily manufactured.

What is claimed is:

1. An optical sensor for directly detecting a chemical substance dissolved or dispersed in water comprising:

at least oneسensing element, at least one light source unit and a first light detector, the sensing element including an optically transparent substrate and a polymer thin film capable of interacting with said chemical substance dissolved or dispersed in water and formed on said substrate and arranged in contact with said water, and wherein the light source unit is positioned on the substrate side of said sensing element, the first light detector is positioned on the substrate side of said sensing element, and said substrate couples light from said light source unit to said polymer thin film at a predetermined angle, and functions as light coupling means for coupling light reflected by said sensing element to said first light detector, and said predetermined incident angle is set at a value smaller than a critical angle of total internal reflection on the interface between said polymer thin film and said water and close to said critical angle.

2. An optical sensor according to claim 1, wherein said chemical substance is organic carbon.

3. An optical sensor according to claim 1, wherein said polymer thin film is made of a material which enables measurement of said chemical substance in accordance with an IER method.

4. An optical sensor according to claim 1, wherein the thickness of said polymer thin film is selected to be less than 10 μm.

5. An optical sensor according to claim 1, wherein said polymer thin film is made of homopolymer or copolymer having a recurring unit represented by the following chemical formula (I):

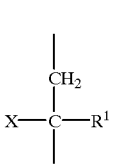

(I)

where X represents —H, —F, —Cl, —Br, —$CH_3$, —$CF_3$, —CN, or —$CH_2$—$CH_3$;

$R^1$ represents —$R^2$ or —Z—$R^2$;

Z represents —O—, —S—, —NH—, —$NR^{2'}$—, —(C=Y)—, —(C=Y)—Y—, —Y—(C=Y)—,

—($SO_2$)—, —Y'—($SO_2$)—, —($SO_2$)—Y'—, —Y'—($SO_2$)—Y'—, —NH—(C=O)—; —(C=O)—NH—, —(C=O)—$NR^{2'}$—, —Y'—(C=Y)—Y'—, or —O—(C=O)—($CH_2$)n—(C=O)—O—;

Y represents the same or different O or S;

Y' represents the same or different O or NH;

n represents an integer ranging from 0 to 20; and $R^2$ and $R^{2'}$ represent the same or different hydrogen, a linear alkyl group, a branched alkyl group, a cycloalkyl group, an un-saturated hydrocarbon group, an aryl group, a saturated or un-saturated hetero ring, or substitutes thereof, said $R^1$ not representing hydrogen, a linear alkyl group, or a branched alkyl group, wherein X is preferably H or $CH_3$; $R^1$ is preferably a substituted or non-substituted aryl group or —Z—$R^2$; Z is preferably —O—, —(C=O)—O—, or —O—(C=O)—; $R^2$ is preferably a linear alkyl group, a branched alkyl group, a cycloalkyl group, an un-saturated hydrocarbon group, an aryl group, a saturated or un-saturated hetero ring, or substitutes thereof.

6. An optical sensor according to claim 5, wherein said polymer thin film is made of a material comprising polymer or copolymer of methacrylic acid esters or acrylic acid esters.

7. An optical sensor according to claim 1, wherein said substrate is a prism.

8. An optical sensor according to claim 1, wherein said substrate is planar and is formed with a grating on a predetermined position thereof.

9. An optical sensor according to claim 1, wherein said substrate is planar, and said sensing element further includes a grating layer formed with a grating, said grating layer disposed between said substrate and said polymer thin film or on a surface of said surface on which said polymer thin film is not formed.

10. An optical sensor according to claim 1, wherein said substrate is planar, and side-coupling is utilized as said light coupling means.

11. An optical sensor according to claim 1, further comprising:

a second light detector for directly receiving light from said light source unit, and an electronic circuit coupled to receive outputs of said first light detector and said second light detector for calculating the ratio of these outputs to generate a signal indicative of the concentration of said chemical substance.

12. An optical sensor according to claim 11, further comprising a housing for holding said light source unit, said first light detector, said second light detector, and said light coupling means in a predetermined positional relationship with respect to said sensing element.

* * * * *

UNITED STATES PATENT AND TRADEMARK OFFICE
CERTIFICATE OF CORRECTION

PATENT NO. : 6,277,330 B1  
DATED : August 21, 2001  
INVENTOR(S) : Yuan Liu, Hironobu Yamamoto and Akihiro Tagaya Page 1 of 1

It is certified that error appears in the above-identified patent and that said Letters Patent is hereby corrected as shown below:

Column 3,  
Line 55, delete "nas" and insert -- has --.

Column 9,  
Line 13, "$\lambda_{c12}$" and insert -- $\theta_{c12}$ --.

Column 10,  
Line 11, delete "$\theta$" and insert -- $\theta c$ --.  
Line 39, delete "$\theta$" and insert -- $\theta c$ --.

Column 13,  
Line 42, delete "6" and insert -- $\theta c$ --.

Column 14,  
Line 17, delete "--" and insert -- -O- --.  
Line 17, delete "-$NR^2$" and insert -- $NR^{2'}$ --.  
Line 20, delete the last occurrence of "-(C=O)-,".

Signed and Sealed this

Seventh Day of May, 2002

*Attest:*

*Attesting Officer*

JAMES E. ROGAN  
*Director of the United States Patent and Trademark Office*